(12) United States Patent
Stenzler et al.

(10) Patent No.: US 7,516,742 B2
(45) Date of Patent: Apr. 14, 2009

(54) METHOD AND APPARATUS FOR DELIVERY OF INHALED NITRIC OXIDE TO SPONTANEOUS-BREATHING AND MECHANICALLY-VENTILATED PATIENTS WITH INTERMITTENT DOSING

(75) Inventors: Alex Stenzler, Long Beach, CA (US); Christopher C. Miller, North Vancouver (CA); Bevin McMullin, North Vancouver (CA)

(73) Assignees: Cardinal Health 207, Inc., Yorba Linda, CA (US); Pulmonox Technologies Corporation, Edmonton, Alberta (CA)

( * ) Notice: Subject to any disclaimer, the term of this patent is extended or adjusted under 35 U.S.C. 154(b) by 270 days.

(21) Appl. No.: 11/234,849

(22) Filed: Sep. 23, 2005

(65) Prior Publication Data
US 2006/0207594 A1 Sep. 21, 2006

Related U.S. Application Data

(63) Continuation-in-part of application No. 10/896,329, filed on Jul. 21, 2004, now abandoned, which is a continuation of application No. 10/348,238, filed on Jan. 21, 2003, now Pat. No. 6,786,217, which is a continuation of application No. 09/449,240, filed on Nov. 24, 1999, now Pat. No. 6,581,599.

(51) Int. Cl.
A61M 16/00 (2006.01)
(52) U.S. Cl. .......................... 128/204.23; 128/204.22; 128/204.21; 128/204.18
(58) Field of Classification Search ............ 128/204.18, 128/204.21, 204.23, 202.22, 203.12, 203.13, 128/203.22
See application file for complete search history.

(56) References Cited

U.S. PATENT DOCUMENTS

| 3,036,584 | A | 5/1962 | Lee |
| 3,192,106 | A | 6/1965 | Bracken et al. |
| 4,127,121 | A | 11/1978 | Westenskow et al. |
| 4,191,952 | A | 3/1980 | Schreiber et al. |

(Continued)

FOREIGN PATENT DOCUMENTS

DE 003713396 A1 11/1998

(Continued)

OTHER PUBLICATIONS

Ray, James D. et al., "A New Method of Preparing Nitric Oxide," Contribution from the Department of Chemistry, Stanford University (1956).

(Continued)

Primary Examiner—Steven O Douglas
(74) Attorney, Agent, or Firm—Sidley Austin LLP

(57) ABSTRACT

A device and method is disclosed for delivering NO to a patient. The device utilizes a single controller that controls two separate flow controllers to deliver an oxygen-containing gas and a NO-containing gas to the patient to provide NO-containing gas at a flow profile that is proportional or quasi-proportional to a flow profile of the oxygen-containing gas throughout patient inspiration. The controller further comprises logic for setting a nitric oxide delivery profile comprising at least two different concentrations of nitric oxide containing gas and for automatically switching between the at least two different concentrations of nitric oxide containing gas on a timed basis.

17 Claims, 15 Drawing Sheets

U.S. PATENT DOCUMENTS

| | | | |
|---|---|---|---|
| 4,224,941 A | 9/1980 | Stivala |
| 4,328,823 A | 5/1982 | Schreiber |
| 4,336,798 A | 6/1982 | Beran |
| 4,345,612 A | 8/1982 | Koni et al. |
| 4,442,856 A | 4/1984 | Betz et al. |
| 4,608,041 A | 8/1986 | Nielsen |
| 4,611,590 A | 9/1986 | Ryschka et al. |
| 4,770,168 A | 9/1988 | Rusz et al. |
| 4,905,685 A | 3/1990 | Olsson et al. |
| 4,954,526 A | 9/1990 | Keefer |
| 5,154,697 A | 10/1992 | Loori |
| 5,155,137 A | 10/1992 | Keefer et al. |
| 5,159,924 A | 11/1992 | Cegielski et al. |
| 5,197,462 A | 3/1993 | Falb et al. |
| 5,396,882 A | 3/1995 | Zapol |
| 5,423,313 A | 6/1995 | Olsson et al. |
| 5,427,797 A | 6/1995 | Frostell et al. |
| 5,485,827 A | 1/1996 | Zapol et al. |
| 5,514,204 A | 5/1996 | Sheu et al. |
| 5,519,020 A | 5/1996 | Smith et al. |
| 5,531,218 A | 7/1996 | Krebs |
| 5,536,241 A | 7/1996 | Zapol |
| 5,558,083 A | 9/1996 | Bathe et al. |
| 5,570,683 A | 11/1996 | Zapol |
| 5,615,669 A | 4/1997 | Olsson et al. |
| 5,632,981 A | 5/1997 | Saavedra et al. |
| 5,648,101 A | 7/1997 | Tawashi |
| 5,650,442 A | 7/1997 | Mitchell et al. |
| 5,651,358 A | 7/1997 | Briend et al. |
| 5,676,963 A | 10/1997 | Keefer et al. |
| 5,688,236 A | 11/1997 | Gragg |
| 5,692,497 A | 12/1997 | Schnitzer et al. |
| 5,700,830 A | 12/1997 | Korthuis et al. |
| 5,713,349 A | 2/1998 | Kearney |
| 5,722,392 A | 3/1998 | Skimming et al. |
| 5,732,693 A | 3/1998 | Bathe et al. |
| 5,765,548 A | 6/1998 | Perry |
| 5,789,447 A | 8/1998 | Wink, Jr. et al. |
| 5,810,795 A | 9/1998 | Westwood |
| 5,814,666 A | 9/1998 | Green et al. |
| 5,814,667 A | 9/1998 | Mitchell et al. |
| 5,823,180 A | 10/1998 | Zapol |
| 5,834,030 A | 11/1998 | Bolton |
| 5,837,736 A | 11/1998 | Mitchell et al. |
| 5,839,433 A | 11/1998 | Higenbottam |
| 5,840,759 A | 11/1998 | Mitchell et al. |
| 5,845,633 A | 12/1998 | Psaros |
| 5,873,359 A | 2/1999 | Zapol et al. |
| 5,885,621 A | 3/1999 | Head et al. |
| 5,904,938 A | 5/1999 | Zapol et al. |
| 5,918,596 A | 7/1999 | Heinonen |
| 5,957,880 A | 9/1999 | Igo et al. |
| 6,000,403 A | 12/1999 | Cantwell |
| 6,060,020 A | 5/2000 | Piuk et al. |
| 6,063,407 A | 5/2000 | Zapol et al. |
| 6,067,983 A | 5/2000 | Stenzler |
| 6,071,254 A | 6/2000 | Augustine |
| 6,073,627 A | 6/2000 | Sunnen |
| 6,083,209 A | 7/2000 | Marasco, Jr. |
| 6,089,229 A | 7/2000 | Bathe et al. |
| 6,103,275 A | 8/2000 | Seitz et al. |
| 6,109,260 A | 8/2000 | Bathe |
| 6,110,895 A | 8/2000 | Rodgers et al. |
| 6,125,846 A | 10/2000 | Bathe et al. |
| 6,131,572 A | 10/2000 | Heinonen |
| 6,142,147 A | 11/2000 | Head et al. |
| 6,158,434 A | 12/2000 | Lugtigheid et al. |
| 6,160,021 A | 12/2000 | Lerner et al. |
| 6,164,276 A | 12/2000 | Bathe et al. |
| 6,190,704 B1 | 2/2001 | Murrell |
| 6,200,558 B1 | 3/2001 | Saavedra et al. |
| 6,232,336 B1 | 5/2001 | Hrabie et al. |
| 6,270,779 B1 | 8/2001 | Fitzhugh et al. |
| 6,358,536 B1 | 3/2002 | Thomas |
| 6,379,660 B1 | 4/2002 | Saavedra et al. |
| 6,432,077 B1 | 8/2002 | Stenzler |
| 6,472,390 B1 | 10/2002 | Stamler et al. |
| 6,494,314 B1 | 12/2002 | Lamborne et al. |
| 6,511,991 B2 | 1/2003 | Hrabie et al. |
| 6,555,058 B2 | 4/2003 | Kamibayashi et al. |
| 6,571,790 B1 | 6/2003 | Weinstein |
| 6,581,599 B1 | 6/2003 | Stenzler |
| 6,601,580 B1 | 8/2003 | Block et al. |
| 6,673,338 B1 | 1/2004 | Arnold et al. |
| 6,703,046 B2 | 3/2004 | Fitzhugh et al. |
| 6,706,274 B2 | 3/2004 | Herrmann et al. |
| 6,715,485 B1 | 4/2004 | Djupesland |
| 6,747,062 B2 | 6/2004 | Murrell |
| 6,750,254 B2 | 6/2004 | Hrabie et al. |
| 6,758,214 B2 | 7/2004 | Fine et al. |
| 6,780,849 B2 | 8/2004 | Herrmann et al. |
| 6,786,217 B2 | 9/2004 | Stenzler |
| 6,793,644 B2 | 9/2004 | Stenzler |
| 6,796,966 B2 | 9/2004 | Thomas |
| 6,811,965 B2 | 11/2004 | Vodovotz et al. |
| 6,867,194 B2 | 3/2005 | Wang et al. |
| 6,887,485 B2 | 5/2005 | Fitzhugh et al. |
| 6,911,478 B2 | 6/2005 | Hrabie et al. |
| 6,920,876 B2 | 7/2005 | Miller et al. |
| 6,938,357 B2 | 9/2005 | Hauch |
| 6,949,530 B2 | 9/2005 | Hrabie et al. |
| 7,048,951 B1 | 5/2006 | Seitz et al. |
| 7,105,502 B2 | 9/2006 | Arnold et al. |
| 7,118,767 B2 | 10/2006 | Kim et al. |
| 7,122,018 B2 | 10/2006 | Stenzler et al. |
| 7,199,154 B2 | 4/2007 | Berthelette et al. |
| 2002/0069877 A1 | 6/2002 | Villareal |
| 2002/0082566 A1 | 6/2002 | Stenzler |
| 2002/0119115 A1 | 8/2002 | Keefer et al. |
| 2002/0138051 A1 | 9/2002 | Hole et al. |
| 2002/0155164 A1 | 10/2002 | Figley et al. |
| 2002/0156416 A1 | 10/2002 | Stenzler |
| 2002/0169202 A1 | 11/2002 | Kazutami et al. |
| 2003/0039697 A1 | 2/2003 | Zhao et al. |
| 2003/0150457 A1 | 8/2003 | Miller et al. |
| 2003/0165578 A1 | 9/2003 | Murrell |
| 2003/0203915 A1 | 10/2003 | Fang et al. |
| 2003/0215528 A1 | 11/2003 | Graham et al. |
| 2003/0228564 A1 | 12/2003 | Edirch et al. |
| 2004/0009238 A1 | 1/2004 | Miller et al. |
| 2004/0043026 A1 | 3/2004 | Tuan et al. |
| 2004/0081580 A1 | 4/2004 | Hole et al. |
| 2004/0112378 A1 | 6/2004 | Djupesland |
| 2004/0131703 A1 | 7/2004 | Bach et al. |
| 2004/0163647 A1 | 8/2004 | Figley et al. |
| 2004/0180863 A1 | 9/2004 | Hrabie et al. |
| 2004/0259840 A1 | 12/2004 | Herrmann et al. |
| 2005/0016427 A1 | 1/2005 | Memory |
| 2005/0079148 A1 | 4/2005 | Fitzhugh et al. |
| 2005/0137521 A1 | 6/2005 | Stenzler |
| 2005/0142217 A1 | 6/2005 | Adams et al. |
| 2005/0148566 A1 | 7/2005 | Waterhouse et al. |
| 2005/0171066 A1 | 8/2005 | Shami |
| 2005/0191372 A1 | 9/2005 | Stenzler et al. |
| 2005/0217668 A1 | 10/2005 | Figley et al. |
| 2005/0217679 A1 | 10/2005 | Miller et al. |
| 2005/0251117 A1 | 11/2005 | Anderson et al. |
| 2005/0265958 A1 | 12/2005 | West et al. |
| 2005/0288260 A1 | 12/2005 | Hrabie et al. |
| 2006/0008529 A1 | 1/2006 | Meyerhoff et al. |
| 2006/0068031 A1 | 3/2006 | Miller et al. |
| 2006/0147553 A1 | 7/2006 | Miller et al. |
| 2007/0065473 A1 | 3/2007 | Miller et al. |
| 2007/0086954 A1 | 4/2007 | Miller et al. |

| | | |
|---|---|---|
| 2007/0088316 A1 | 4/2007 | Stenzler et al. |
| 2007/0104653 A1 | 5/2007 | Miller et al. |

FOREIGN PATENT DOCUMENTS

| | | |
|---|---|---|
| EP | 0640356 A1 | 3/1995 |
| EP | 0640357 A1 | 3/1995 |
| EP | 0659445 A1 | 6/1995 |
| EP | 0659445 B1 | 6/1995 |
| EP | 1243278 A2 | 9/2002 |
| FR | 2656218 | 6/1991 |
| JP | 3-139364 | 6/1991 |
| JP | 3-207365 | 9/1991 |
| KR | 202066 | 6/1999 |
| WO | WO 92/17445 | 10/1992 |
| WO | WO 93/15779 | 8/1993 |
| WO | WO 93/17741 | 9/1993 |
| WO | WO 95/09612 | 4/1995 |
| WO | WO 96/00006 | 1/1996 |
| WO | WO 96/22803 | 8/1996 |
| WO | WO 96/25184 | 8/1996 |
| WO | WO 96/31217 | 10/1996 |
| WO | WO 98/01142 | 1/1998 |
| WO | WO 99/49921 | 10/1999 |
| WO | WO 00/07653 | 2/2000 |
| WO | WO 00/30659 | 6/2000 |
| WO | WO 01/65935 A1 | 9/2001 |
| WO | WO 02/056864 A2 | 7/2002 |
| WO | WO 03/066109 A1 | 8/2003 |
| WO | WO 2005/060603 A3 | 7/2005 |
| WO | WO 2005/110052 A3 | 11/2005 |
| WO | WO 2005/110441 A2 | 11/2005 |

OTHER PUBLICATIONS

Shank, J. L. et al., "The Effect of Nitric Oxide on Bacteria," Applied Microbio, No. 10, 189-189 (1962).
Norman, C. et al., "Nitrogen Oxides in Tobacco Smoke," Nature, vol. 205, No. 4971, pp. 915-916, (Feb. 1965).
Canetti, G., "Present aspects of bacterial resistance in tuberculosis," Am. Rev. Respir. Dis. 92:687-703 (1965).
Bass, H. et al., "Regional structure and function in brochiectasis," Am. Rev. Respir. Dis. 97:598-609 (1968).
Contractor, A. M. et al., "Development and Evaluation of an Inhalation Aerosol of Nitroglycerin," Journal of Pharmaceutical Sciences, vol. 63, No. 6, pp. 907-911 (Jun. 1974).
Oda, H. et al., "Nitrosyl-Hemoglobin Formation in the Blood of Animals Exposed to Nitric Oxide," Archives of Environmental Health, vol. 30, No. 7, pp. 453-456 (Sep. 1975).
Katsuki, S. et al., "Stimulation of Guanylate Cyclase by Sodium Nitroprusside, Nitroglycerin and Nitric Oxide in Various Tissue Preparations and Comparison to the Effects of Sodium Azide and Hydroxylamine," Journal of Cyclic Nucleotide Research, vol. 3, pp. 23-25 (1977).
Hugod, C., "Effect of exposure of 43 PPM nitric oxide and 3.6 PPM nitrogen dioxide on rabbit lung," Arch. Occup. Environ. Health 42:159-167 (1979).
Yoshida, J. et al., "Metabolic Fate of Nitric Oxide," Int Arch Occup Environ Health, vol. 46, No. 1, pp. 71-77 (Apr. 1980).
Borland, C., "The Fate of Inhaled Nitric Oxide," Clinical Science, Abstract No. 104, p. 37P (1983).
Mancinelli et al., "Effects of Nitric Oxide and Nitrogen Dioxide on Bacterial Growth," Applied and Environmental Microbiology, vol. 46, No. 1, pp. 198-202 (Jul. 1983).
Demling, R. H. et al., "The Pulmonary and Systemic Response to Recurrent Endotoxemia in the Adult Sheep," Surgery, vol. 100, No. 5, pp. 876-883 (Nov. 1986).
Higenbottam, T., "Primary Pulmonary Hypertension," British Medical Journal, vol. 293, pp. 1456-1457 (Dec. 1986).
Higenbottam, T. et al., "Primary Pulmonary Hypertension," British Medical Journal, vol. 294, p. 705 (Mar. 1987).
Palmer, R.M.J. et al., "Nitric Oxide Release Accounts for the Biological Activity of Endothelium-Derived Relaxing Factor," Nature, vol. 327, pp. 524-526 (Jun. 1987).

Ignarro, L. J. et al., "Endothelium-Derived Relaxing Factor Produced and Released From Artery and Vein is Nitric Oxide," Proceedings of the National Academy of Sciences of the United States of America, vol. 84, No. 24, pp. 9265-9269 (Dec. 1987).
Higenbottam, T. W. et al., "Inhaled 'Endothelium Derived-Relaxing Factor' (EDRF) in Primary Hypertension (PPH)," Abstract, American Review of Respiratory Disease, Suppl., vol. 137, No. 4, Part 2, p. 107 (Apr. 1988).
Ignarro, L. J. et al., "Endothelium-Derived Relaxing Factor and Nitric Oxide Possess Identical Pharmacologic Properties as Relaxants of Bovine Arterial and Venous Smooth Muscle," The Journal of Pharmacology and Experimental Therapeutics, vol. 246, No. 1, pp.
Dinh-Xuan, A. T. et al., "Non-Prostanoid Endothelium-Derived Vasoactive Factors," The Journal of International Medical Research, vol. 17, pp. 305-315 (1989).
Borland, C. D. R. et al., "A Simultaneous Single Breath Measurement of Pulmonary Diffusing Capacity with Nitric Oxide and Carbon Monoxide," The European Respiratory Journal, vol. 2, No. 1, pp. 56-63 (Jan. 1989).
Buga, G. M. et al., "Endothelium-Derived Nitric Oxide Relaxes Nonvascular Smooth Muscle," European Journal of Pharmacology, vol. 161, No. 1, pp. 61-72, (Feb. 1989).
Garg, U. C. et al., "Nitric Oxide-generating Vasodilators and 8-Bromo-Cyclic Guanosine Monophosphate Inhibit Mitogensis and Proliferation of Cultured Rat Vascular Smooth Muscle Cells," The Journal of Clinical Investigation, vol. 83, No. 5, pp. 1774-1777 (May 1989).
Meyer, M. et al., "Nitric Oxide (NO), a New Test Gas for Study of Alveolar-capillary Diffusion," The European Respiratory Journal, vol. 2, No. 6, pp. 494-496 (Jun. 1989).
Dinh-Xuan, A. T. et al., "Primary Pulmonary Hypertension: Diagnosis, Medical and Surgical Treatment," vol. 84, pp. 189-197 (1990).
Stavert, D. M. et al., "Nitric Oxide and Nitrogen Dioxide as Inducers of Acute Pulmonary Injury When Inhaled at Relatively High Concetrations for Brief Periods," Inhalation Toxicology 2:53-67 (1990).
Moinard, J. et al., "Determination of Lung Capillary Blood Volume and Membrane Diffusing capacity in Patients with COLD using the NO-CO Method," The European Respiratory Journal, vol. 3, pp. 318-322 (1990).
Archer, S. L., "Comparison of the Hemodynamic Effects of Nitric Oxide and Endothelium-Dependent Vasodilators in Intact Lungs," Journal of Applied Physiology, vol. 68, No. 2, pp. 735-747 (Feb. 1990).
Meyer, M. et al., "Pulmonary Diffusing Capacities for Nitric Oxide and carbon Monoxide Determined by Rebreathing in Dogs," Journal of Applied Physiology, vol. 68, No. 6, pp. 2344-2357 (Jun. 1990).
Vane, J. R. et al., "Regulatory Functions of the Vascular Endothelium," The New England Journal of Medicine, vol. 323, No. 1, pp. 27-36 (Jul. 1990).
Higenbottam, T. et al., "Has the Treatment of Asthma Improved?" Chest, vol. 98, No. 3, pp. 706-712 (Sep. 1990).
Swami, A. et al., "The Pulmonary Physician and critical Care: 2. The Injury Lung: Conventional and Novel Respiratory Therapy," Thorax, vol. 47, pp. 555-562 (1992).
Bult, H. et al., "Chronic Exposure to Exogenous Nitric Oxide May Suppress its Endogenous Release and Efficacy," Journal of Cardiovascular Pharmacology, vol. 17, Suppl. 3, pp. S79-S82 (1991).
Frostell, C. et al., "Inhaled Nitric Oxide, A Selective Pulmonary Vasodilator Reversing Hypoxic Pulmonary Vasoconstriction," Circulation Journal of the American Heart Association, vol. 83, pp. 2083-2047 (1991).
Hendrickson, D.A. et al, "Regents and Stains," Manual of Clinical Microbiology, 5th Ed., American Society for Microbiology, pp. 1289-1314 (1991).
Cremona, g. et al., "Endothelium-derived Relaxing Factor and the Pulmonary Circulation," Lung, vol. 169, pp. 185-202 (1991).
Falke, K. et al., "Inhaled Nitric Oxide Selectively Reduces Pulmonary Hypertension in Severe ARDS and Improves Gas Exchange as well as right Heart Ejection fraction—A Case Report," Abstract 248, Am. Rev. Respir. Dis., vol. 143 (1991).

Fratacci, M. D., "Inhaled Nitric Oxide—A Selective Pulmonary Vasodilator of Heparin-Protamine Vasoconstriction in Sheep," Anesthesiology, vol. 75, pp. 990-999 (1991).

Denis, M., "Interferon—Gamma-treated Murine Macrophages Inhibit Growth of Tubercle Bacilli via the Generation of Reactive Nitrogen Intermediates," Cellular Immunology, vol. 132, No. 1, pp. 150-157 (Jan 1991).

Dinh-Xuan, A. T. et al., "Impairment of Endothelium-Dependent Pulmonary-Artery Relaxation in Chronic Obstructive Lung Disease," The New England Journal of Medicine, vol. 324, No. 22, pp. 1539-1547 (May 1991).

Frostell, C. et al., "Inhaled Nitric Oxide—A Selective Pulmonary Vasodilator Reversing Hypoxic Pulmonary Vasoconstriction," Circulation, vol. 83, No. 6 (Jun. 1991).

Moncada, S. et al., "Nitric Oxide: Physiology, Pathophysiology, and Pharmacology," Pharmacological Reviews, vol. 43, No. 2 (Jun. 1991).

Frostell, C. et al., "Inhaled Nitric Oxide Dilates Human Hypoxic Pulmonary Vasoconstriction Without Causing Systemic Vasodilation," Anesthesiology, The Journal of The American Society of Anesthesiologists, Inc., vol. 75, No. 3A, Abstract A989 (Sep. 1991).

Girard, C. et al., "Inhaled Nitric Oxide (NO) in Pulmonary Hypertension Following Mitral Valve Replacement," Anesthesiology, The Journal of The American Society of Anesthesiologists, Inc., vol. 75, No. 3A, Abstract A983 (Sep. 1991).

Roberts, J. D. et al., "Inhaled Nitric Oxide (NO): A Selective Pulmonary Vasodilator for the Treatment of Persistent Pulmonary Hypertension on the Newborn (PPHN)," Abstract 1279, Circulation, vol. 84, No. 4, p. II-321 (Oct. 1991).

Pepke-Zaba, J. et al., "Inhaled Nitric Oxide as a Cause of Selective Pulmonary Vasodilatation in Pulmonary Hypertension," The Lancet, vol. 338, No. 8776, pp. 1173-1174 (Nov. 1991).

Radomski, M. W., et al., "Human Colorectal Adenocarcinoma Cells: Differential Nitric Oxide Synthesis Determines Their Ability to Aggregate Platelets," Cancer Research, vol. 51, pp. 6073-6078 (Nov. 15, 1991).

Johns, R. A., "EDRF/Nitric Oxide—The Endogenous Nitrovasodilator and a New cellular Messenger," Anesthesiology, The Journal of The American Society of Anesthesiologists, Inc., vol. 75, No. 6, pp. 927-931 (Dec. 1991).

Pearl, R. G., "The Pulmonary Circulation," Anesthesiology, vol. 5, pp. 848-854 (1992).

Chan, J. et al., "Killing of the Virulent Mycobacterium Tuberculosis by Reactive Nitrogen Intermediates Produced by Activated Murine Macophages," J. Exp. Med. 175:1111-1122 (Apr. 1992).

Rossiant, R. et al., "Successful Treatment of Severe Adult Respiratory Distress Syndrome with Inhaled Nitric Oxide," American Review of Respiratory Disease, Suppl., vol. 145, No. 4, Part 2, p. A80 (Apr. 1992).

Rossiant, R. et al., "Inhaled Nitric Oxide in Contrast to Infused Prostacyclin Selectively Reduces Pulmonary Hypertension and Improves Gas Exchange in Severe ARDS," Abstract, American Review of Respiratory Disease, Suppl., vol. 145, No. 4, Part 2, p. A185.

Bigatello, L. M., "Inhaled Nitric Oxide is a Selective Pulmonary Vasodilator in Septic Patients with Severe ARDS," Abstract, American Review of Respiratory Disease, Suppl., vol. 145, No. 4, Part 2, p. A185 (Apr. 1992).

Snyder, S. H. et al., Biological Roles of Nitric Oxide, Scientific American, vol. 266, No. 5, pp. 68-77 (May 1992).

Foubert, L., "Safety Guidelines for Use of Nitric Oxide," The Lancet, vol. 339, No. 8809, pp. 1615-1616 (Jun. 1992).

Messent, M. et al., "Pharmacotherapy in Lung Injury," Thorax, vol. 47, No. 7, pp. 651-656 (Jul. 1992).

Barash, P. et al., "Anesthesiology," The Journal of the American Medical Association, vol. 268, No. 3, pp. 335-337 (Jul. 1992).

Dupuy, P. M. et al., "Bronchodilator Action of Inhaled Nitric Oxide in Guinea Pigs," J. Clin. Invest., vol. 90, pp. 421-428 (Aug. 1992).

Kinsella, J. P. et al., "Hemodynamic Effects of Exogenous Nitric Oxide in Ovine Transitional Pulmonary Circulation," American Journal of Physiology: Heart and Circulatory Physiology, vol. 32, No. 3, pp. H875-H880 (Sep. 1992).

Roberts, J. D. et al., "Inhaled Nitric Oxide in Persistent Pulmonary Hypertension of the Newborn," The Lancet, vol. 340, pp. 818-819 (Oct. 1992).

Kinsella, J. P. et al., "Low-Dose Inhalational Nitric Oxide in Persistent Pulmonary Hypertension of the Newborn," The Lancet, vol. 340, pp. 819-820 (Oct. 1992).

Girard, C. et al., "Inhaled Nitric Oxide After Mitral Valve Replacement in Patients with Chronic Pulmonary Artery Hypertension," Anesthesiology, The Journal of the American Society of Anesthesiologists, Inc., vol. 77, No. 5, pp. 880-883 (Nov. 1992).

Kacmarek, R. M., "Nitric Oxide as a Bronchodilator in Methacholine Induced Bronchospasm in Mild Asthmatics," Abstract (1993).

Blomqvist, H. et al., "Enhanced Pneumonia Resolution by Inhalation of Nitric Oxide?" Acta Anaesthesiol Scand, vol. 37, pp. 110-114 (1993).

Buga, G. M. et al., "Negative Feedback Regulation of Endothelial Cell Function by Nitric Oxide," Circulation Research, Journal of the American Heart Association, 73:808-812 (1993).

Higenbottam, T., "Inhaled Nitric Oxide: A Magic Bullet?" Quarterly Journal of Medicine, vol. 86, pp. 555-558 (1993).

Stenqvist, O. et al., "Evaluation of a New System for Ventilatory Administration of Nitric Oxide," Acta Anaesthesiologica Scandinavica, pp. 687-691 (1993).

Rossaint, R. et al., "Inhaled Nitric Oxide For The Adult Respiratory Distress Syndrome," New England Journal of Medicine, vol. 328, pp. 399-405 (Feb. 1993).

Maragos, C. M., et al., "Nitric Oxide/Nucleophile Complexes Inhibit the in Vitro Proliferation of A375 Melanoma Cells via Nitric Oxide Release," Cancer Research, vol. 53, pp. 564-568 (Feb. 1, 1993).

Pearl, R. G., "Inhaled Nitric Oxide—The Past, The Present and the Future," Anesthesiology, vol. 78, No. 3, pp. 413-416 (Mar. 1993).

Assreuy, J. et al., "Feedback Inhibition of Nitric Oxide Synthase Activity by Nitric Oxide," British Journal of Pharmacology, vol. 108, pp. 883-837 (Mar. 1993).

Higenbottam, T. et al., "Highlights on Pulmonary Hypertension: A Commentary," The European Respiratory Journal, vol. 6, No. 7, pp. 932-933 (Jul. 1993).

Haworth, S. G., "Pulmonary Hypertension in Childhood," The European Respiratory Journal, vol. 6, No. 7, pp. 1037-1043 (Jul. 1993).

Higenbottam, T. et al., "Acute and Chronic Hypoxic Pulmonary Hypertension," The European Respiratory Journal, vol. 6, No. 8, pp. 1207-1212 (Sep. 1993).

Mansch, R. et al., "Simulation of Microbiologically and chemically Influenced corrosion of Natural Sandstone," Abstract, ASTM Special Technical Publication, 203-16; 1 pg. (1994).

Lowenstein, C. J. et al., "Nitric Oxide: a Physiologic Messenger," Annals of Internal Medicine, vol. 120, Issue 3, pp. 227-237 (Feb. 1994).

Dong, Z., et al., "Inverse Correlation Between Expression of Inducible Nitric Oxide Synthase Activity and Production of Metastasis in K-1735 Murine Melanoma Cells," Cancer Research, vol. 54, pp. 789-793 (Feb. 1, 1994).

Butt, A. Y. et al., "New Therapies for Primary Pulmonary Hypertension," Chest, vol. 105, No. 2, pp. 21S-25S (Feb. 1994).

Foubert, L. et al., "Nitric Oxide in Pulmonary Hypertension: Therapeutic Considerations," Journal of Cardiothoracic and Vascular Anesthesia, vol. 8, No. 3, Suppl. 2, p. 41 (Jun. 1994).

Snow, D. et al., "Inhaled Nitric Oxide in Pulmonary Hypertension," Journal of Cardiothoracic and Vascular Anesthesia, vol. 8, No. 3, Suppl. 2, Abstract No. 127 (Jun. 1994).

O'Brien, L. et al., Strains of Mycobacterium Tuberculosis Differ in Susceptibility to Reactive Nitrogen Intermediates In Vitro, Infection and Immunity, vol. 62, No. 11, pp. 5187-5190 (Aug. 1994).

Young, J. D., "A Universal Nitric Oxide Delivery System," British Journal of Anaesthesia, vol. 73, No. 4, pp. 700-702 (Oct. 1994).

Hagenah, Jens-Uwe, "The Use of Nitric Oxide (NO) in Intensive Care Ventilation," Dragerwerk Aktiengesellscha, pp. 1 and 3-36.

Hanson, S. R., et al., "Nitric Oxide Donors: A Continuing Opportunity in Drug Design," Nitric Oxide Biochemistry, Molecular Biology, and Therapeutic Implications, Advances in Pharmacology, vol. 34, pp. 383-398 (1995).

Chan, J. et al., "Effects of Nitric Oxide Synthase Inhibitors on Murine Infection with Mycobacterium Tuberculosis," Infection and Immunity, vol. 63, No. 2., pp. 736-740 (Feb. 1995).

DeGroote, M. A., et al., "NO Inhibitions: Antimicrobial Properties of Nitric Oxide," Clincial Infectious Diseases, vol. 21, Suppl. 2, pp. S162-S165 (Oct. 1995).

Body, S. C., M.D. et al., "Nitric Oxide: Delivery, Measurement, and Clinical Application," Journal of Cardiothoracic and Vascular Anesthesia, vol. 9, No. 6, pp. 748-763 (Dec. 1995).

Higenbottam, T. et al., "The Treatment of Primary Pulmonary Hypertension," Therapeutic Applications of Iloprost, A Volume in the Clinical Monograph Series, pp. 35-41 (Apr. 1995).

Szabo, C., "The Pathophysiological Role of Peroxynitrite in Shock, Inflammation and Ischemia-Reperfusion Injury," Shock, vol. 6, No. 2, pp. 79-88 (1996).

Higenbottam, T., "Nitric Oxide and the Lung," Horizons in Medicine, No. 7 pp. 203-224 (1996).

Young, J. D. et al., "Delivery and Monitoring of Inhaled Nitric Oxide," Intensive Care Medicine, vol. 22, No. 1, pp. 77-86 (Jan. 1996).

Mellgren, K., et al., "Nitric Oxide in the Oxygenator Sweep Gas Reduces Platelet Activation During Experimental Perfusion," The Annals of Thoracic Surgery, vol. 61, No. 4, pp. 1194-1198 (Apr. 1996).

Ramnarine, S. I., et al., "Nitric Oxide Inhibition of Basal and Neurogenic Mucus Secretion in Feerrete Trachea in Vitro," British Journal of Pharmacology, vol. 118 (4), pp. 998-1002 (Jun. 1996).

Channick, R. N., M.D. et al., "Pulsed Delivery of Inhaled Nitric Oxide to Patients with Primary Pulmonary Hypertension," Chest, The Cardiopulmonary and Critical Care Journal, vol. 109, No. 6, pp. 1545-1549 (Jun. 1996).

Hudome, S. M., M.D. et al., "Precise Control of Nitric Oxide Concentration in the Inspired Gas of Continuous Flow Respiratory Devices," Pediatric Pulmonology, vol. 22, No. 3, pp. 182-187 (Sep. 1996).

Cuthbertson, B. H. et al., "Inhaled Nitric Oxide," The Lancet, vol. 348, No. 9039, pp. 1447-1448 (Nov. 1996).

Gerlach, H. et al., "Low Levels of Inhaled Nitric Oxide in Acute Lung Injury," Nitric Oxide and the Lung, vol. 98, Chapter 14, pp. 271-283 (1997).

Dupuy, P. M. et al., "Bronchial Effects of Nitric Oxide," Nitric Oxide and the Lung, vol. 98, Chapter 15, pp. 285-311 (1997).

Leopold, J. A. et al., "New Developments in Nitrosovasodilator Therapy," Vascular Medicine, vol. 2, No. 3 (1997).

Rook, G. A. W., "Intractable Mycobacterial Infections Associated with Genetic Defects in the Receptor for Interferon Gamma: What Does This Tell Us About Immunity to Mycobacteria?" Thorax, vol. 52 (Suppl. 3), pp. S41-S46 (1997).

Katayama, Y. et al., "Inhaled Nitric Oxide and Arterial Oxygen Tension in Patients with chronic Obstructive Pulmonary Disease and Severe Pulmonary Hypertension," Thorax, The Journal of the British Thoracic Society, vol. 52, pp. 120-124 (1997).

Neonatal Inhaled Nitric Oxide Study Group, "Inhaled Nitric Oxide in Full-Term and Nearly Full-Term Infants with Hypoxic Respiratory Failure," New England Journal of Medicine, 336(9):597-604 (Feb. 1997).

Roberts, J. D. et al., "Inhaled Nitric Oxide and Persistent Pulmonary Hypertension of the Newborn," New England Journal of Medicine, 336:605-610 (Feb. 1997).

Imanaka, H., M.D. et al., "Inaccuracies of Nitric Oxide Delivery Systems During Adult Mechanical Ventilation," Anesthesiology, vol. 86, No. 3, pp. 676-688 (Mar. 1997).

Marriott, H. et al., "The Role of Nitric Oxide in Respiratory Disease," Schweiz Med Wochenschr, vol. 127, pp. 709-714 (Apr. 1997).

Nozaki, Y. et al., "Mechanism of Nitric Oxide-Dependent Killing of Mycobacterium bovis BCG in Human Alveolar Macrophages," Infection and Immunity, vol. 65, pp. 3644-3647 (Sep. 1997).

Hess, D., RRT, Ph.D. et al., "Delivery Systems for Inhaled Nitric Oxide," Respiratory Care Clinics of North America, vol. 3, No. 3, pp. 371-410 (Sep. 1997).

Hoehn, T., M.D. et al., "Effect of Therapeutic Concentrations of Nitric Oxide on Bacterial Grown in Vitro," Crit Care Med, vol. 26, No. 11, pp. 1857-1862 (1998).

Bauer, J. A. et al., Evaluation of Linear Polyethylenei-mine/Nitric Oxide Adduct on Wound Repair: Therapy Versus Toxicity, The Wound Healing Society, pp. 569-577 (1998).

Pizzichini, M. M. M. et al., "Asthma and Natural Colds: Inflammatory Indices in Induced Sputum: A Feasibility Study," American Journal of Respiratory Critical Care Medicine, vol. 158, pp. 1178-1184 (1998).

Higenbottam, T. et al., "Primary and Secondary Pulmonary Hypertension," Seminars in Respiratory and Critical Care Medicine, vol. 19, No. 1, pp. 91-95 (1998).

Long, R. et al., "Pulmonary Tuberculosis Treated with Directly Observed Therapy: Serial Changes in Lung Structure and Function," Chest, vol. 113, pp. 933-943 (1998).

Klein, M.D. et al., "Nitric Oxide Delivery Systems," Acta Anaesthesiologica Scandinavica, pp. 274-275 (1998).

Francoe, M, RRT et al., "Inhaled Nitric Oxide: Technical Aspects of Administration and Monitoring," Critical Care Medicine, vol. 26, No. 4, pp. 782-796 (Apr. 1998).

Keefer, L. K., "Nitric Oxide-Releasing Compounds: From Basic Research to Promising Drugs," The American Chemical Society, vol. 28, pp. 30-35 (Aug. 1998).

Ivy, D. D., M.D. et al., "Acute Hemodynamic Effects of Pulsed Delivery of Low Flow Nasal Nitric Oxide in Children with Pulmonary Hypertension," The Journal of Pediatrics, vol. 133, No. 3, pp. 453-456 (Sep. 1998).

Hiesmayr, M. J. et al., "Performance of Proportional and Continuous Nitric Oxide Delivery Systems During Pressure- and Volume-Controlled Ventilation," The British Journal of Anaesthesia, vol. 81, No. 4, pp. 544-552 (Oct. 1998).

Katayama, Y., M.D. et al., "Minimizing the Inhaled Dose of NO With Breath-by-Breath Delivery of Spikes of Concentrated Gas," Circulation, Journal of the American Heart Association, vol. 98, No. 22 (Dec. 1998).

Higenbottam, T. et al., "Treatments for Severe Pulmonary Hypertension," The Lancet, vol. 353, No. 9150, pp. 338-340 (Jan. 1999).

Long, R. et al., "Mycobateriocidal Action of Exogenous Nitric Oxide," Antimicrobial Agents and Chemotherapy, vol. 43, No. 2, pp. 403-405, (Feb. 1999).

Schofnagl, H. et al., "Proportional and Continuous NO Delivery Systems," British Journal of Anaesthesia, vol. 82, No. 4, pp. 647-653 (Apr. 1999).

Rimmelzwaan, G. F. et al., "Inhibition of Influenza Virus Replication by Nitric Oxide," Journal of Virology, American Society for Microbiology, vol. 73, No. 10, pp. 8880-8883 (Oct. 1999).

Webert, K. E., M.D. et al., "Effects of Inhaled Nitric Oxide In A Rate Model of *Pseudomonas ceruginosa* Pneumonia," Crit Car Med, vol. 28, No. 7, pp. 2397-2405 (2000).

Tamaoki, J., M.D., et al., "Impairment of Airway Mucociliary Transport in Patients with Sinobronchial Syndrome: Role of Nitric Oxide," Journal of Aerosol Medicine, vol. 13, No. 3, pp. 239-244 (Nov. 2000).

Long et al., "Treatment of Sputum-Smear Positive Pulmonary Tuberculosis With Inhaled Nitric Oxide," 2001-Abstract Form to the ATS 2001 San Francisco, May 18-23, 2001 (faxed Mar. 27, 2001).

Frank, S., et al., "Nitric Oxide Drives Skin Repair: Novel Functions Of An Established Mediator," Kidney International, vol. 61, pp. 882-888 (2002).

Imada, M., et al., "Functional Roles of Nasal Nitric Oxide in Nasal Patency and Mucociliary Function," ACTA Oto-Laryngologica, vol. 122, No. 5, pp. 513-519 (Jul. 2002).

Kirov, M. Y. M.D., et al., "Combination of Intravenously Infused Methylene Blue and Inhaled Nitric Oxide Ameliorates Endotoxin-Induced Lung Injury in Awake Sheep," Critical Care Medicine, vol. 31, No. 1, pp. 179-186 (Jan. 2003).

Shami, P. J., et al., JS-K, A Glutathione/Glutathione S-Transferase-activated Nitric Oxide Donor of the Diazeniumdiolate Class with Potent Antineoplastic Activity, Molecular Cancer Therapeutics, vol. 2, pp. 409-417 (Apr. 2003).

Counter-Defendant's First Amended Responses to Counterclaimant's Second Set of Interrogatories Relating to Counterclaims (Nos. 19-38) (Oct. 2003).

Miller, Chris C. et al.; "Treatment of Chronic Nonhealing Leg Ulceration with Gaseous Nitric Oxide: A Case Study"; Journal of Cutaneous Medicine and Surgery, pp. 233-238 (2004).

Vijh, A. K., "High Infectious Burden, Low Cancer Incidence, and Early Malignancy in Developing Countries: A Molecular Hypothesis in Term of the Role of Nitric Oxide," Medical Hypotheses, vol. 63, pp. 208-210 (Feb. 2004).

Sanders, S. P. et al., "Role of Nasal Nitric Oxide in the Resolution of Experimental Rhinovirus Infection," Journal of Allergy and Clinical Immunology, vol. 113, No. 4, pp. 697-702 (Apr. 2004).

Schmidt, I. et al., Physiologic and Proteomic Evidence for a Role of Nitric Oxide in Biofilm Formation by *Nitrosomonas europaea* and Other Ammonia Oxidizers; Journal of Bacteriology, vol. 186, No. 9, pp. 2781-2788 (May 2004).

Reynolds, M. M., et al., "Nitric Oxide-Releasing Hydrophobic Polymers: Preparation, Characterization, and Potential Biomedical Applications," Free Radical Biology & Medicine, The Official Journal for the Society for Free Radical Biology and Medicine, vol. 37, No. 7, pp. 926-936 (Oct. 2004).

Lechner, M., et al., "Inducible Nitric Oxide Synthase (iNOS) in Tumor Biology: The Two Sides of the Same Coin," Seminars in Cancer Biology, vol. 15, pp. 277-289 (2005).

Ghaffair, A., et al., "A Direct Nitric Oxide Gas Delivery System for Bacterial and Mammalian Cell Cultures," Nitric Oxide Biology and Chemistry, vol. 12, pp. 129-140 (2005).

Proud, D., "Nitric Oxide and The Common Cold," Journal of Allergy and Clinical Immunology, vol. 5, pp. 37-42 (2005).

Nablo, B. J., et al., Inhibition of Implant-Associated Infections Via Nitric Oxide Release, Science Direct, Biomaterials, vol. 26, pp. 6984-6990 (May 2005).

McMullin, B. B., MSc RRT, et al., "The Antimicrobial Effect of Nitric Oxide on the Bacteria That Cause Nosocomial Pneumonia in Mechanically Ventilated Patients in the Intensive Care Unit," Respiratory Care, vol. 50, No. 11, pp. 1451-1456 (Nov. 2005).

Hurford, W. E.; Nitric Oxide As A Bacterial Agent: Is The Cure Worse Than The Disease?; Respiratory Care, vol. 50, No. 11, pp. 1428-1429 (Nov. 2005).

Katayama, Y. et al., "A Minimal Dose of Inhaled Nitric Oxide Delivered As A 'Spike' of Small Volume in Early Inhalation," Section of Respiratory Medicine, Division of Clinical Sciences, The Medical School, University of Sheffield (23 pages).

Turchi, J. J., "Nitric Oxide and Cisplatin Resistance: NO Easy Answers," PNAS, vol. 103, No. 12, pp. 4337-4338 (Mar. 21, 2006).

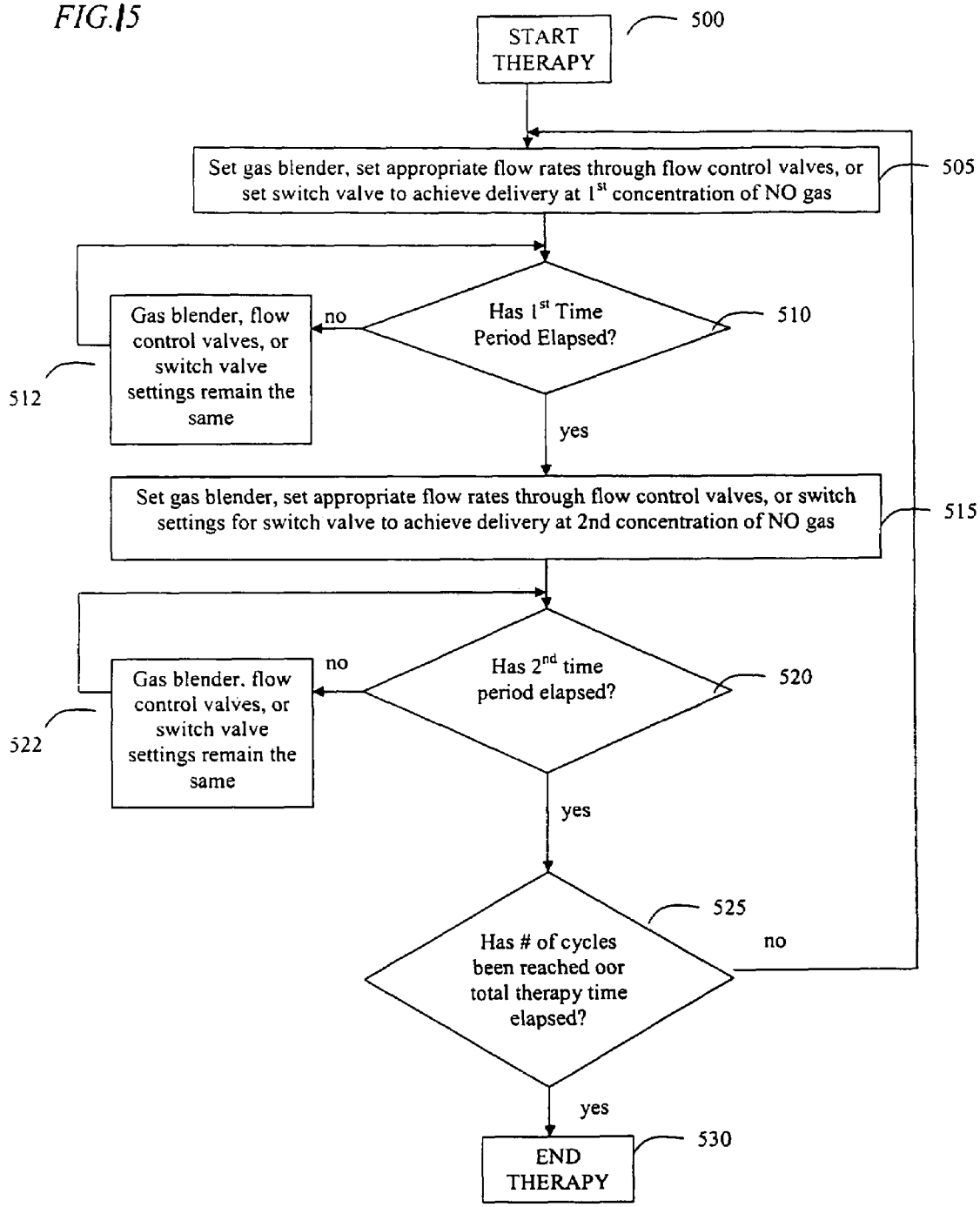

METHOD AND APPARATUS FOR DELIVERY OF INHALED NITRIC OXIDE TO SPONTANEOUS-BREATHING AND MECHANICALLY-VENTILATED PATIENTS WITH INTERMITTENT DOSING

This application is a continuation-in-part of PCT Application No. US2005/016427, filed May 11, 2005 and U.S. patent application Ser. No. 10/896,329 filed Jul. 21, 2004 now abandoned, which is a continuation of U.S. patent application Ser. No. 10/348,238 filed on Jan. 21, 2003 now U.S. Pat. No. 6,786,217, which is a continuation of U.S. patent application Ser. No. 09/449,240 issued on Nov. 24, 1999 now U.S. Pat. No. 6,581,599, which are all hereby incorporated by reference in their entirety.

FIELD OF THE INVENTION

The field of the present invention relates to methods and devices for delivery of exogenous or gaseous nitric oxide gas to mammals.

BACKGROUND OF THE INVENTION

NO is an environmental pollutant produced as a byproduct of combustion. At high concentrations (generally at or above 1000 ppm), NO is toxic. NO also is a naturally occurring gas that is produced by the endothelium tissue of the respiratory system. In the 1980's, it was discovered by researchers that the endothelium tissue of the human body produced NO, and that NO is an endogenous vasodilator, namely, an agent that widens the internal diameter of blood vessels.

With this discovery, numerous researchers have investigated the use of low concentrations of inhaled NO to treat various pulmonary diseases in human patients. See Higenbottam et al., Am. Rev. Resp. Dis. Suppl. 137:107, 1988. It was determined, for example, that PPH can be treated by inhalation of low concentrations of NO. With respect to pulmonary hypertension, inhaled NO has been found to decrease pulmonary artery pressure (PAP) as well as pulmonary vascular resistance (PVR).

Prior to the advent of NO inhalation therapy, pulmonary hypertension was treated by the administration of drugs known as systemic vasodilators. These drugs, such as prostacyclin, nitroprusside, hydroalazine, and calcium channel blockers suffered from the limitation that the drugs, by their nature, produced systemic effects. For example, the drugs not only decreased PAP levels, but also systemic blood pressure.

Unlike systemic vasodilators, inhaled NO acts as a selective pulmonary vasodilator, acting primarily on the endothelium tissue of the lung. Upon inhalation, NO is absorbed into the capillary blood in the precapillary airspaces and alveolar capillaries. Inhaled NO has negligible action beyond the site of its uptake since NO is rapidly inactivated by the reaction with hemoglobin to form methemoglobin.

The use of inhaled NO for PPH patients was quickly followed by the use of inhaled NO for other respiratory diseases. For example, NO has been investigated for the treatment of patients with increased airway resistance as a result of emphysema, chronic bronchitis, asthma, adult respiratory distress syndrome (ARDS), and chronic obstructive pulmonary disease, (COPD). Still other respiratory diseases where NO inhalation therapy is thought to be beneficial include, by way of illustration and not by way of limitation: allograft lung transplantation, ischemia-reperfusion injury, congestive heart failure, septic shock, and high-altitude pulmonary edema.

While NO has shown promising preliminary results with respect to the treatment and prevention of the diseases mentioned above, delivery methods and devices must cope with certain problems inherent with gaseous NO delivery. First, exposure to high concentrations of NO is toxic. NO is toxic in high concentrations, especially over 1000 ppm. Even lower levels of NO can be harmful if the time exposure is relatively high. For example, the Occupational Safety and Health Administration (OSHA) has set exposure limits for NO in the workplace at 25 ppm time-weighted average for eight (8) hours. Typically, NO is administrated to patients in the concentration range of about 1 ppm to about 100 ppm.

Another problem with the delivery of NO is that NO rapidly oxidizes in the presence of oxygen to form $NO_2$, which is highly toxic, even at low levels. For example, OSHA has set exposure limits for $NO_2$ at 5 ppm. In any NO delivery device it is thus desirous to reduce, to the largest extent possible, the conversion of NO to $NO_2$. The rate of oxidation of NO to $NO_2$ is dependent on numerous factors, including the concentration of NO, the concentration of $O_2$, and the time available for reaction. One problem with the inhalation of NO is that when NO is therapeutically inhaled, it is often mixed with high concentrations of $O_2$. Consequently, this increases the conversion rate of NO to $NO_2$. It is thus preferable to minimize the contact time between NO and $O_2$ when the NO is combined with a source of oxygen gas.

Methods and devices for delivering NO to a patient have been developed to minimize the conversion of NO to $NO_2$. For example, with respect to the delivery of NO to patients connected to a mechanical ventilator, the $NO/NO_2$ stream has been introduced directly into the respiratory limb of a patient. See Martin Francoe, et al., "*Inhaled Nitric Oxide: Technical Aspects of Administration and Monitoring,*" Critical Care Medicine, Vol. 26, No. 4, pp. 785-87 April 1998. This arrangement has the advantage over other designs that combine and mix $NO/NO_2$ and $Air/O_2$ prior to their input to the ventilator since the contact time between NO and $O_2$ is reduced.

Another delivery method and device that reduces the exposure to $O_2$ and to a certain extent NO is disclosed in the U.S. Pat. No. 5,839,433 issued to Higenbottam. The '433 patent discloses a method and apparatus for supplying NO to a patient. According to the '433 patent, a very short pulse of NO is delivered intermittently, either at the start or end of inspiration. The '433 patent thus teaches the delivery of a bolus or plug of nitric oxide to the patient by administering a very short pulse of NO during inspiration. The timing of the delivery (beginning vs. late) is altered depending on the disease that is to be treated. When NO is desired in the lowermost depths of the lungs, for example, during treatment of pulmonary hypertension where NO acts on the small pulmonary arteries and capillaries, a short pulse is given at the beginning of inspiration. On the other hand, for asthma-like airway diseases, a very short pulse is administered near the end of inspiration. This method attempts to deliver NO to the desired location of the lungs. The method reduces the total exposure of the lungs to NO as well as reduces the total amount of NO available to react with $O_2$ to form toxic $NO_2$.

The pulses of NO delivered according to the '433 patent are of a predetermined width, which can be altered by changing the amount of time that a control valve is left open. The '433 patent, however, fails to disclose the proportional delivery of NO gas to the patient having a flow profile that tracks or is proportional or quasi-proportional to the flow profile of an oxygen-containing gas. Rather, the valve mechanism provides a bolus, or square wave-type "plug" of NO to the patient, the length of which, is altered by adjusting its width (i.e., holding the valve in the open position for a longer period of time). In this regard, the pulse has the flow profile of a square wave regardless of the profile of the patient's inspiration profile.

Generally, NO is administered to patients that are either spontaneously breathing or connected to a mechanical ventilator. In spontaneously breathing patients, a patient typically wears a tight fitting mask, transtracheal $O_2$ catheter, nasal cannula, or other tubing passing directly into the airway of a patient. NO is typically mixed with $O_2$ and air prior to introduction into the patient airway. See Dean Hess, Ph.D., et al., "*Delivery Systems for Inhaled Nitric Oxide,*" Respiratory Care Clinics of North America, Vol. 3, No. 3, pp. 402-404 September 1997. These spontaneous systems, however, suffer from the limitation that the NO concentration can fluctuate within a relatively wide range. The dose of NO varies with the patient's ventilatory pattern due to the fact that the patient's inspiration profile changes on a breath-by-breath basis. The delivered dose of NO is thus approximated from assumptions regarding the patient's ventilatory pattern.

There are several different methods of delivering NO to a mechanically-ventilated patient. In one method, the $NO/N_2$ stream is premixed with $Air/O_2$ prior to entering the ventilator. While such pre-mixing may better permit the inspired concentration of NO to be controlled, the production of $NO_2$ is significantly higher given the longer contact time between NO and $O_2$. This is particularly true for ventilators with large internal volumes.

In another method of delivery, NO is continuously injected into the inspiratory limb of the ventilator circuit. This method, however, has difficulty maintaining a stable NO concentration throughout the entire inspiration flow. Moreover, when continuously injected NO is used with adult ventilators that have phasic flow patterns (flow only during inspiration), the inspiratory circuit fills with NO during expiration, and a large bolus of NO is delivered to the patient in the next breath. See, e.g., Dean Hess, Ph.D., et al., "*Delivery Systems for Inhaled Nitric Oxide,*" Respiratory Care Clinics of North America, Vol. 3, No. 3, p. 381 September 1997. This method may result in an inspired NO concentration that may be more than double the calculated or estimated dose. In addition, the concentration of delivered NO varies with the length of the patient's expiration. For example, when the expiratory time is short, the delivered NO concentration is lower due to less time for filling the inspiratory limb with NO.

Yet another method of delivering NO involves intermittent injections of an NO-containing gas into the patient's inspiratory limb. In this regard, NO is delivered into the inspiratory limb only during the inspiratory phase. For this method to be acceptable, however, the flow from the ventilator must be continuously and precisely measured, and the injected does of NO must be precisely titrated such that the delivered NO and inspiratory flow waveform are not affected. See, Dean Hess, Ph.D., et al., "*Delivery Systems for Inhaled Nitric Oxide,*" Respiratory Care Clinics of North America, Vol. 3, No. 3, p. 384, September 1997.

One such commercial device operating on the above-mentioned intermittent injection principle is the I-NOvent Delivery System (Ohmeda). In the I-NOvent Delivery System a device separate and apart from the mechanical ventilator injects NO directly into the inspiration circuit of the patient. Flow in the inspiration limb of the circuit is measured via a flow sensor and NO is injected in proportion to the measured flow to provide the desired dose. See, Dean Hess, Ph.D., et al., "*Delivery Systems for Inhaled Nitric Oxide,*" Respiratory Care Clinics of North America, Vol. 3, No. 3, p. 395, September 1997.

Another commercial device utilizing intermittent injection of NO is the NOdomo device (Dragerwerk, Germany). The NOdomo device interfaces, like the I-NOvent Delivery System, with a separate mechanical ventilator. NO addition is controlled via a mass flow controller, adding a proportion of NO into the breathing circuit. Unlike the I-NOvent Delivery System, however, the NOdomo device controls NO flow delivery from an electronic flow controller that receives an input signal directly from the ventilator. See, Dean Hess, Ph.D., et al., "*Delivery Systems for Inhaled Nitric Oxide,*" Respiratory Care Clinics of North America, Vol. 3, No. 3, p. 399 September 1997.

U.S. Pat. No. 5,558,083 issued to Bathe et al. discloses a NO delivery system. The delivery system can be used with a mechanical ventilator as well as a gas proportioning device for spontaneous-breathing. A CPU controls a proportional control valve that is in-line with a source of NO gas. The CPU calculates the desired flow from, among other things, the flow of breathing gas measured via a flow sensor 46 and NO concentration measured by NO sensor 65. The proportional control valve 24 is controlled to arrive at the desired NO concentration.

In a second embodiment of the Bathe et al. device, a supplemental supply of $O_2$ 74 is connected to the NO line. A proportional control valve 78 is positioned in-line with the $O_2$ supply 74 and reports to the CPU 56. As disclosed in the '083 patent, the $O_2$ is provided as a safety measure should the $O_2$ level fall below a critical level. Col. 8, lines 50-61. In the event that the level of $O_2$ has dropped below the minimum threshold, the CPU 56 directs the proportional flow controller to increase the flow of $O_2$ to the $NO/N_2$ stream.

The '083 patent, however, fails to teach or suggest the proportional-type control of $NO/N_2$, or $O_2$ to track or match the flow of either $O_2$ or the inspiration profile of a patient. Rather, the $O_2$ is used as a safety measure should the $O_2$ concentration fall below a threshold value. Moreover, in the devices disclosed in the '083 and '433 patents, residual NO gas is left in the device/inspiration limb between breaths.

It is thus desirous to have a device and method of delivery of NO to a patient that can control the delivery of an NO-containing gas as well as an oxygen-containing gas to a patient via a single controller. The device preferably can provide either a constant concentration of NO to the patient during inspiration or a non-constant concentration of NO to the patient depending on the desired setting. In addition, the device preferably does not suffer from the limitation of other delivery systems, where NO may remain in the system between breaths. Namely, the device and method preferably eliminates any bolus or residue of NO-containing gas that might build-up between breaths.

In addition to its effects on pulmonary vasculature, NO may also be introduced as a anti-microbial agent against pathogens via inhalation or by topical application. See e.g., WO 00/30659, U.S. Pat. No. 6,432,077, which are hereby incorporate by reference in their entirety. The application of gaseous nitric oxide to inhibit or kill pathogens is thought to be beneficial given the rise of numerous antibiotic resistant bacteria. For example, patients with pneumonia (often acquired through use of a ventilator, e.g., VAP) may not respond to antibiotics given the rise of antibiotic resistant strains associated with these conditions.

Clinical use of nitric oxide for inhalation has conventionally been limited to low concentration of nitric oxide given the potential toxicity. The toxicity may stem from binding of nitric oxide to hemoglobin that give rise methemoglobin or from the conversion of nitric oxide gas to nitrogen dioxide (NO2). However, to overwhelm pathogenic defense mechanisms to nitric oxide, it is desirable to deliver nitric oxide at a higher concentration (e.g., between 150 ppm to 250 ppm, and even to 400 ppm) than has traditionally been used clinically for inhalation. Thus, a need exists for a delivery method that is effective against combating pathogens and minimizing the risk of toxicity.

SUMMARY OF THE INVENTION

The present invention provides for the intermittent dosing and delivery of nitric oxide in combination with the use of the patient's respiratory flow profile during the periods of nitric oxide delivery. It is envisioned that a method and device delivering intermittent high doses of nitric oxide for a period of time and which cycles between high and low concentration of nitric oxide is desirable, useful, and overcomes the problems of toxicity. The high concentration of nitric oxide is preferably delivered intermittently for brief periods of time that are interspersed with periods of time with either no nitric oxide delivery or lower concentrations of nitric oxide. This keeps the exposure to the high concentrations of nitric oxide required to overwhelm the nitric oxide defense mechanisms of the pathogens to an average level that is safe for humans to inhale.

In a preferred embodiment, high concentration of nitric oxide may be delivered at a concentration between 80 ppm to 300 ppm, preferably between 150 ppm to 250 ppm, and more preferably between 160 ppm to 200 ppm. Low concentration of nitric oxide preferably is delivered at a concentration between zero (0) ppm to 80 ppm, and preferably at a concentration of 20 ppm to 40 ppm.

The time periods may vary and in a wide range that preferably will deliver a dose of x time of 600 to 1000 ppmhrs per day. For example, the method would deliver 160 ppm for 30 minutes every four hours with 20 ppm delivered for the 3.5 hours between the higher concentration delivery. High concentration may also be delivered for a period of time between 10 minutes to 45 minutes, and the low concentration is preferably delivered for a period of time longer than the period of time in which the high concentration is delivered. However, it may also be delivered for the same length of time as the high concentration of nitric oxide with less number of cycles to achieve substantially the same amount of ppmhrs of nitric oxide per day. Thus, the high and low concentrations are alternately delivered, and the cycling of the delivery can be for a day, two days, three days, or any other time prescribed by a physician.

The delivery of nitric oxide gas based on the patient's respiratory flow profile that is used in combination with the intermittent dosing can be accomplished in a number of ways. In a first embodiment, a method of delivering a steady concentration of NO to a spontaneously breathing patient via delivery means is disclosed. The method includes the step of detecting the onset of inspiration by the patient. The inspiration flow profile is determined for an individual breath. An oxygen-containing gas is supplied to the delivery means, wherein the oxygen-containing gas has a flow profile that tracks the inspiration flow profile. A NO-containing gas is supplied to the delivery means, wherein the NO-containing gas has a flow profile that is proportionally less than the flow profile of the oxygen-containing gas throughout inspiration.

In a second embodiment, a method of delivering a non-constant concentration of nitric oxide to a spontaneously breathing patient via delivery means is disclosed. The method includes the steps of the first aspect, however, the NO-containing gas is supplied to the delivery means wherein the NO-containing gas has a flow profile that is less than, but closely tracks the oxygen-containing gas flow profile at the beginning of inspiration, and wherein the difference between the flow profile of the oxygen-containing gas and the flow profile of the nitric oxide-containing gas progressively increases through the remainder of inspiration.

In a third embodiment, another method of delivering a non-constant concentration of nitric oxide to a spontaneously breathing patient via delivery means is disclosed. The method includes the steps of the first aspect, however, the nitric oxide-containing gas has a flow profile that is substantially less than the oxygen-containing gas flow profile at the beginning of inspiration compared to the end of inspiration, and wherein the difference between the flow profile of the oxygen-containing gas and the flow profile of the nitric oxide-containing gas progressively decreases throughout the remainder of inspiration.

In yet another embodiment, a method of delivering a constant concentration of nitric oxide to a mechanically-ventilated patient via single controller is disclosed. In the method, the desired inspiration flow profile is set in the controller. The flow rate of an oxygen-containing gas is varied in accordance with the inspiration flow profile by delivering a first signal from said controller to a first control valve controlling the rate of flow of an oxygen-containing gas to the patient, thereby creating a flow profile of oxygen-containing gas. The flow rate of a nitric oxide-containing gas is varied in accordance with the inspiration profile by delivering a second signal from said controller to a second control valve controlling the rate of flow of the nitric oxide-containing gas to the patient, creating a flow profile of nitric oxide-containing gas. The nitric oxide-containing flow profile is less than and proportional to the flow profile of the oxygen-containing gas throughout patient inspiration.

In still another embodiment, a method of delivering a non-constant concentration of NO to a mechanically-ventilated patient is disclosed. The method includes the steps of the previously recited method, however, the flow rate of the nitric oxide-containing gas is varied to create a flow profile of nitric oxide-containing gas that is less than, but closely tracks the oxygen-containing gas flow profile in the beginning of the inspiration, wherein the difference between the flow profiles of the oxygen-containing gas and the nitric oxide-containing gas progressively increases through the remainder of inspiration.

In yet another method for delivering a non-constant concentration of NO to a mechanically-ventilated patient, the flow rate of the nitric oxide-containing gas has a flow profile that is substantially less than the oxygen-containing gas flow profile at the beginning of inspiration, and wherein the difference between the flow profile of the oxygen-containing gas and the nitric oxide-containing gas progressively decreases throughout the remainder of inspiration.

In another embodiment, a method of delivering nitric oxide via delivery means to a mechanically or spontaneously breathing patient having a certain inspiration profile is disclosed. The method includes the aspect of an air flush to eliminate remaining nitric oxide or enriched oxygen. The method includes the step of supplying in a first breath a mixture of oxygen-containing gas and a nitric oxide-containing gas to the delivery means, the oxygen-containing gas and a nitric oxide-containing gas having a flow profile proportional or quasi proportional to the inspiration flow profile. In at least one next breath, a source of enriched oxygen-containing gas is supplied having a flow profile that is proportional or quasi-proportional to the inspiration flow profile. A source of air is supplied at or near the end of the first and next breaths to flush the delivery means of enriched oxygen and nitric oxide.

In another embodiment, a method of delivering nitric oxide to a spontaneously breathing patient via delivery means is disclosed. The method includes the step of detecting the onset of inspiration. An oxygen-containing gas is supplied to the delivery means, wherein the oxygen-containing gas has a pre-programmed flow profile. A nitric oxide-containing gas is supplied to the delivery means, wherein the nitric oxide-containing gas has a pre-programmed flow profile that is proportional or quasi-proportional to the flow profile of the oxygen-containing gas throughout inspiration.

In another aspect of the invention, different embodiments of a delivery device are disclosed for practicing the methods set-forth above. The device can be designed in a number of ways to combine the ability to deliver intermittent dosing of nitric oxide with delivery based on the patient's respiratory flow profile.

In one embodiment, a device for delivering nitric oxide to a patient is disclosed. The device includes a source of an oxygen-containing gas connected via tubing to a patient inspiration interface device. A source of a nitric oxide-containing gas is connected via tubing to the patient inspiration interface device. A first proportional flow controller is located between the source of oxygen-containing gas and the patient inspiration interface device for varying the flow rate of the oxygen-containing gas to the patient inspiration interface device. A second proportional flow controller is located between the source of nitric oxide-containing gas and the patient inspiration interface device for varying the flow rate of the nitric oxide-containing gas to the patient inspiration interface device. An inspiration flow profile sensor is provided for detecting the onset of inspiration of the patient. The device includes a controller for controlling the first and second proportional flow controllers in response to the detection of the onset of inspiration from the inspiration flow profile sensor, the first and second proportional flow controllers being controlled such that the nitric oxide-containing gas has pre-programmed flow profile that is proportional or quasi-proportional to the flow profile of the oxygen-containing gas throughout inspiration.

The device may additionally nitric oxide analyzer and timer in which the concentration of nitric oxide delivered is automatically changed on a timed basis to a concentration set by the operator and for a set period of time defined by the operator. The device would include logic (e.g. software or firmware) that allows for setting of two different nitric oxide concentrations and with separate time settings for the delivery of each concentration.

Alternatively, the device may also include two sources of nitric oxide gas, in which one source provides the high concentration of nitric oxide and the other source provides the low concentration of nitric oxide. A switch valve (preferably electronically controlled) is then provided to switch the flow of nitric oxide gas from the high concentration to the low concentration, or vice versa, based on a predefined time. A third source of diluent gas may also be provided to dilute the nitric oxide gas.

BRIEF DESCRIPTION OF THE DRAWINGS

FIGS. 11-13 illustrate schematic representations of various embodiments of a nitric oxide delivery device according to one aspect of the present invention.

FIG. 15 illustrates the logic for delivering alternating high and low concentrations of nitric oxide gas.

DETAILED DESCRIPTION OF THE PREFERRED EMBODIMENT

Figure 1:
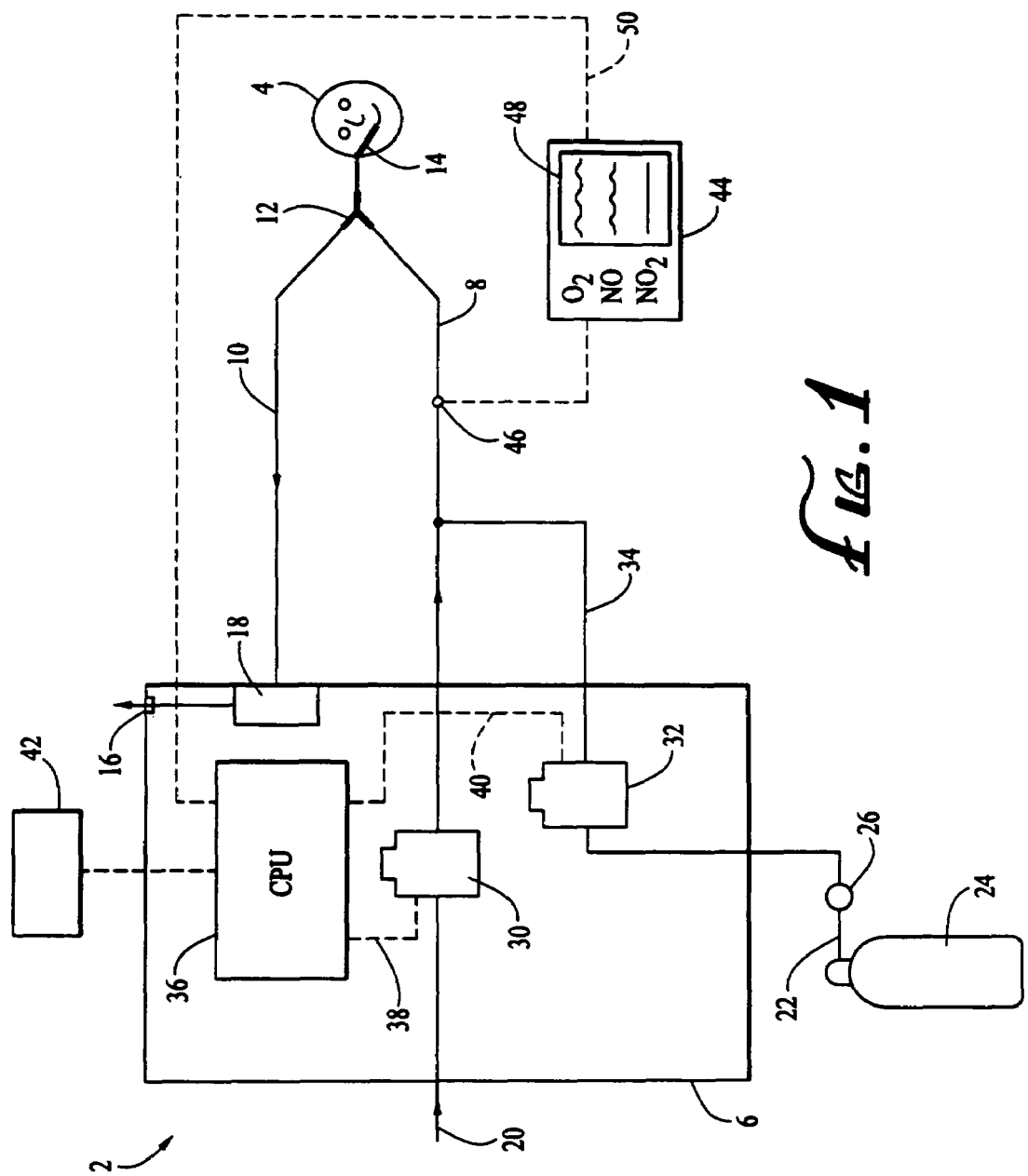
FIG. 1 is a schematic illustration of the device being used with a patient supported by mechanical ventilation.

Referring now to the Figures, FIG. 1 shows a schematic representation of the device 2 for delivering NO gas to a patient 4 connected to a mechanical ventilator 6. In this embodiment of the invention, the device 2 is the mechanical ventilator 6 since both control of patient inspiration, expiration, and delivery of NO are all controlled by the device 2. In this regard, a separate NO administration device is not needed since the device 2/mechanical ventilator 6 delivers to NO gas to the patient 4.

As seen in FIG. 1, the device 2 includes an inspiration limb 8 and an expiration limb 10. The inspiration limb 8 and the expiration limb 10 are connected via a Y-piece 12. The Y-piece 12 connects to delivery means for delivering the gaseous mixture to the patient 4. The delivery means preferably includes a patient inspiration interface device 14. The patient inspiration interface device 14 can be any number of devices that connect a generally hollow, tubular construction (i.e., flexible tubing) to the respiratory tract of the patient 4. For example, by way of illustration and not by limitation, the patient inspiration interface device 14 can include a tube for intubation into the patient's 4 airway, a nasal cannula, a face mask, or a transtracheal catheter. Flexible, hollow tubing is typically used in the inspiration limb 8 and expiration limb 10. The expiration limb 10 returns to the device 2 where the expired gases pass through an exhaust port 16. The expired gas can be vented to directly to the atmosphere, or alternatively, the expired gas can pass through an optional gas scavenger system 18 to remove NO and $NO_2$ from the expiration gas prior to atmospheric venting.

The inspiration limb 8 is attached to the other end of the Y-piece 12 and serves as a transport medium for the sources of oxygen-containing gas 20 and NO-containing gas 22 to the patient 4. The source of oxygen-containing gas 20 can come from any number of sources, including, for example, atmospheric air, compressed air, compressed air enriched with oxygen, and a mixture of oxygen and $N_2$. The main requirement for the oxygen-containing gas 20 is that the gas contain at least some component of oxygen. Typically, when the device 2 is connected to a patient 4, the oxygen-containing gas 20 is delivered to the device via a dedicated line in a medical facility having a pre-set oxygen concentration. Alternatively, the oxygen-containing gas 20 can be delivered via a pressurized cylinder.

The source of NO-containing gas 22 is shown in FIG. 1 as being a pressurized cylinder 24 containing NO gas. While the use of a pressurized cylinder 24 is the preferable method of storing the NO-containing gas 22, other storage and delivery means, such as a dedicated feed line (wall supply), can also be used. Typically, the NO-containing gas 22 is a mixture of $N_2$ and NO. While $N_2$ is typically used to dilute the concentration of NO, any inert gas can also be used. When the NO-containing gas 22 is stored in pressurized cylinder 24, it is preferable that the concentration of NO in the pressurized cylinder 24 fall within the range of about 800 ppm to about 1200 ppm. Commercial nitric oxide manufacturers typically produce nitric oxide mixtures for medical use at around the 1000 ppm range. Extremely high concentrations of NO are undesirable because accidental leakage of NO gas is more hazardous, and high partial pressures of NO tends to cause the spontaneous degradation of NO into nitrogen.

While the inspiration concentration of NO gas generally falls within the range of about 1 ppm to about 100 ppm, it is preferable to use a source of NO-containing gas 22 at a higher concentration for several reasons. First, it is generally not possible to special-order or purchase pressurized cylinders 24 containing NO at a requested concentration. While it is possible to create pressurized cylinders 24 with lower concentrations of NO by mixing with an additional volume of inert gas, this process is time consuming, adds additional cost, and has the potential of introducing oxygen into the gas mixture. U.S. Pat. No. 5,839,433 issued to Higenbottam, for example, utilizes a low concentration source of NO. (100 ppm NO cylinder). Pressurized cylinders 24 with low concentrations of NO are also not as desirable from an economic standpoint. Since a smaller quantity of NO is contained within pressured cylinders 24 having low NO concentrations (i.e., 100 ppm), these pressurized cylinders 24 exhaust their supply of NO much more quickly than a pressurized cylinder 24 containing a higher concentration of NO. Consequently, low NO ppm pressurized cylinders 24 are changed more frequently than pressurized cylinders 24 having a larger concentration of NO. This increases the overall cost of the NO treatment.

Since the pressure in the pressurized cylinder 24 is relatively high compared to the pressure of the breathing gas, a pressure regulator 26 is preferably employed to reduce the pressure of the NO-containing gas 22 prior to introduction to the ventilator 4.

The device 2 further includes a first control valve 30 that is located in-line between the oxygen-containing gas 20 and the inspiration limb 8. The first control valve 30 thus receives the oxygen-containing gas 20 at an input port and modulates, or controls the flow of the oxygen-containing gas 20 into the inspiration limb 8 through a second export port. The first control valve 30 can include, for example, a proportional control valve that opens (or closes) in a progressively increasing (or decreasing if closing) manner depending on an electronic input. As another example, the first control valve 30 can also include a mass flow controller. The first control valve 30 can include any number of control valves that can quickly and accurately alter the flow rate of a gas across a relatively wide range of flow rates.

The output of the first control valve 30 leads to the inspiration limb 8 of the patient 4. In this regard, the first control valve 30 controls the inspiration profile of the oxygen-containing gas 20. The inspiration profile of the oxygen-containing gas 20 is the flow rate of the oxygen-containing gas 20 as a function of inspiration time. The inspiration profile of the oxygen-containing gas 20 can be seen in FIG. 2(a).

Still referring to FIG. 1, a second control valve 32 is located in-line between the NO-containing gas 22 and the inspiration limb 8. The second control valve 32 thus receives the NO-containing gas 22 at an input port and modulates, or controls the flow of the NO-containing gas 22 into the inspiration limb 8 through a second export port. The second control valve 32 can include, for example, a proportional control valve that opens (or closes) in a progressively increasing (or decreasing if closing) manner depending on an electronic input. As another example, the second control valve 32 can also include a mass flow controller. The second control valve 32 can include any number of control valves that can quickly and accurately alter the flow rate of a gas across a relatively wide range of flow rates. Like the first control valve 30, the inspiration profile of the second control valve 32 controls the inspiration profile of the NO-containing gas 22. The inspiration profile of the NO-containing gas 22 is the flow rate of the NO-containing gas 22 as a function of time.

Exiting the second control valve 32 is a NO-addition line 34 that enters the inspiration limb 8. The NO-addition line 34 thus carries the controlled flow of NO-containing gas 22 to the inspiration limb 8. Preferably, the NO-addition line 34 can enter the inspiration limb 8 at any point between the ventilator 6 and the patient inspiration interface device 14. Most preferably, the NO-addition line 34 enters the inspiration limb 8 at a location that is prior to the Y-piece 12. When an optional gas monitor 44, described more fully below, is included as part of the device 2 to measure the concentration of inspired gases in the inspiration limb 8, the NO-addition line 34 preferably enters the inspiration limb 8 upstream of the location where the gas concentration measurements are made. Even more preferably, the NO-addition line 34 enters the inspiration limb 8 upstream of where the gas concentration measurements are made at a distance that is equal to, or greater than, six-times the internal diameter of the tubing used in the inspiration limb 8.

The device further includes CPU 36. The CPU 36 acts as a controller of the first and second control valves 30, 32. The CPU 36 sends, via signal lines 38, 40, signals to control the opening and closing of the control valves 30, 32. As one option, the CPU 36 contains preset instructions on controlling the inspiration profiles of the oxygen-containing gas 20 and the NO-containing gas 22. The instructions can be stored in read-only-memory (ROM) on the CPU 36, or alternatively, the instructions can be input to the CPU 36 via an input device 42. The input device 42 can be any number of devices that encode the flow profiles of the oxygen-containing gas 20 and the NO-containing gas 22. These include, by way of illustration, and not by way of limitation: a computer, a diskette, a control panel, and the like.

The input device 42 can input, for example, the set-point concentration of NO in the breathing gas. The desired set-point concentration of NO is typically set by a physician, for example. The input device 42 can thus alter the degree of proportionality between the flow profile of the oxygen-containing gas 20 and the flow profile of the NO-containing gas 22. A higher degree of proportionality (i.e., the flow profile of the NO-containing gas 22 more closely tracks the flow profile of the oxygen-containing gas 20) would generally produce a higher concentration of inspired NO. The degree of proportionality also affects the timing of the NO gas purge.

The input device 42 may also input gas purge parameters to the CPU 36 to determine when the flow profile of the NO-containing gas 22 is truncated. This can be done, for example, by establishing a time after inspiration is started at which the flow profile of the NO-containing gas 22 is dropped to zero. Alternatively, the NO-containing gas 22 can terminate once the flow rate of the oxygen-containing gas 20 drops below a certain pre-set level. These settings can be input to the CPU 36 via the input device 42.

By modulating the flow rates of both the oxygen-containing gas 20 and the NO-containing gas 22, the CPU 36 controls the inspiration flow profile of each breath of the patient. The CPU 36 can create any number of inspiration flow profiles. For example, the CPU 36 can deliver a sine-shaped, square-shaped, or ramp-shaped inspiration flow profile. Of course, other inspiration flow profiles other than those specifically mentioned-above can also be delivered to the patient 4. The CPU 36 can also control other parameters such as the respiratory rate, tidal volume, and inspiration pressure settings. These parameters can be sent to the CPU 36 via input device 42.

The present invention contemplates using a CPU 36 that gives the device 2 complete programmability. In this regard, the flow profiles of the both the oxygen-containing gas 20 and the NO-containing gas 22 can be controlled during a single breath. While proportional and quasi-proportional flow profiles are disclosed in greater detail herein, it should be appreciated that any flow profile (of the oxygen-containing gas 20 or the NO-containing gas 22) can be produced for a single breath of a patient 4. Complete programmability is also possible where the device employs input device 42.

While CPU 36 is shown as the preferred controller for controlling the flow profiles of the oxygen-containing gas 20 and the NO-containing gas 22, the present invention further contemplates using an analog switching mechanism (not shown) as an alternative controller.

Figure 2A:
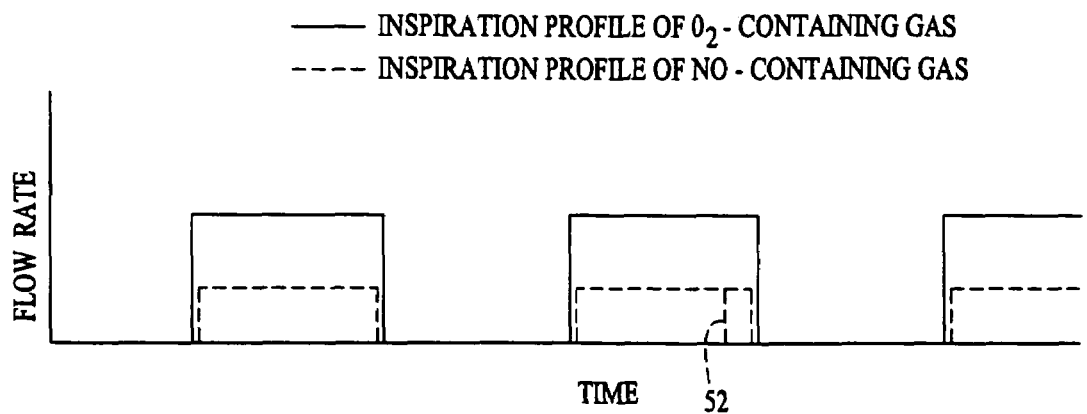
FIG. 2(a) illustrates a square-shaped inspiration profile of the oxygen-containing gas and the NO-containing gas for delivering a constant concentration of NO to a patient.
Figure 2B:
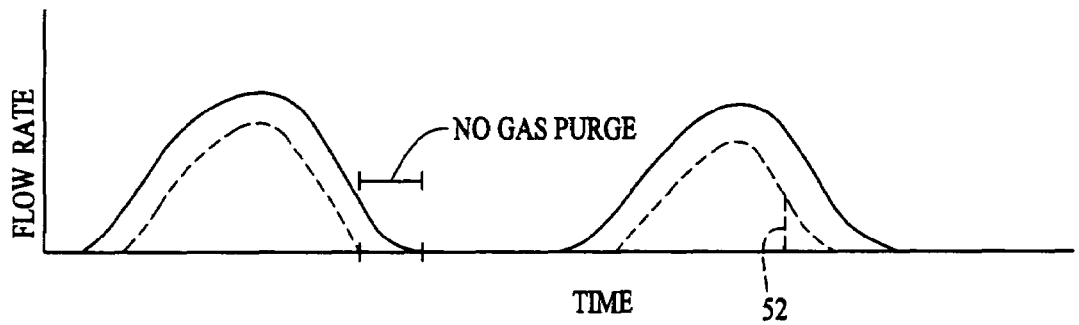
FIG. 2(b) illustrates a sine-shaped inspiration profile of the oxygen-containing gas and the NO-containing gas for delivering a constant concentration of NO to a patient.

A description of the method of operation of the device 2 will now be given. In the standard continuous mandatory ventilation mode, the device 2 delivers to a patient 4 a preset tidal volume at a predetermined respiratory rate. The inspiration flow profile that is desired (e.g., sine, square, or ramp) is delivered to the patient 4 by administering an oxygen-containing gas 20 and an NO-containing gas 22 that have flow profiles that are similar to the inspiration flow profile that is desired. FIGS. 2(a)-2(b) show the flow profiles of the oxygen-containing and NO-containing gases 20, 22. As can best be seen in FIG. 2(a), the flow profile of the NO-containing gas 22 is proportional to the flow profile of the oxygen-containing gas 20. Proportional is meant to indicate that the flow rate of the NO-containing gas 22 is less than, but proportionally tracks the flow profile of the oxygen-containing gas 20 throughout the patient's inspiration (the exception to this being the optional truncation of NO flow as described more fully below). In this regard, the delivered gas mixture of NO and oxygen has near constant concentration. The patient 4 thus receives a steady concentration of NO throughout inspiration.

The proportional flow is accomplished via the single CPU 36. The CPU 36 sends signals to the first and second controller valves 30, 32 to keep the flow of the NO-containing gas 22 lower, but in proportion to the flow of the oxygen-containing gas 20. Since a single CPU 36 is used to control both the first and second control valves 30, 32, there is no need to measure and report back to a control unit, the flow rate of either the NO-containing gas stream 22 or the oxygen-containing gas stream 20 via a flow sensor or the like.

Figure 2C:
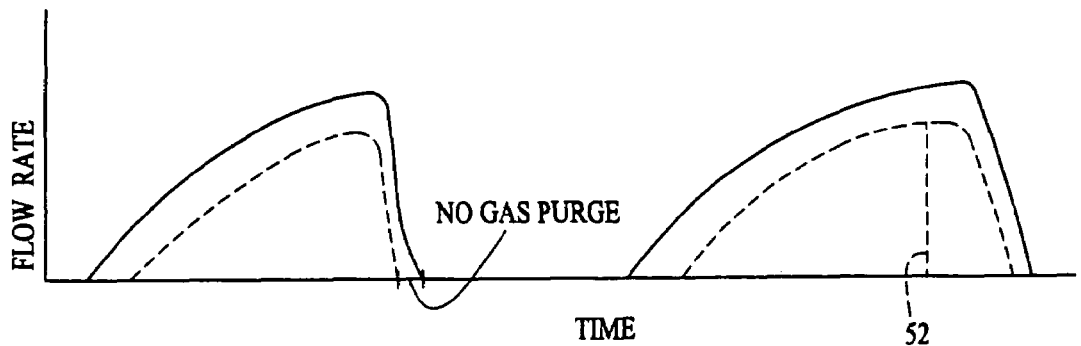
FIG. 2(c) illustrates a ramp-shaped inspiration profile of the oxygen-containing gas and the NO-containing gas for delivering a constant concentration of NO to a patient.

The proportional flow control also has the benefit of purging the inspiration limb 8 of NO-containing gas 22 during certain inspiration flow patterns. For example, as seen in FIGS. 2(b) & 2(c), the flow rate of the NO-containing gas 22 reaches zero near the end portion of inspiration while the oxygen-containing gas 20 continues to have positive flow. In this regard, the flow of oxygen-containing gas 20 purges the inspiration limb 8 of NO until the next breath.

Alternatively, the CPU 36 can send a close-valve signal to the second control valve 32 near the end of patient inspiration. This close-valve signal truncates the flow profile (the truncated flow profile 52 is shown in FIGS. 2(a)-(c)) of the NO-containing gas 22 and leaves the oxygen-containing gas 20 as the only flow. The oxygen-containing gas 20 thus purges the inspiration limb 8 of NO.

Figure 3A:
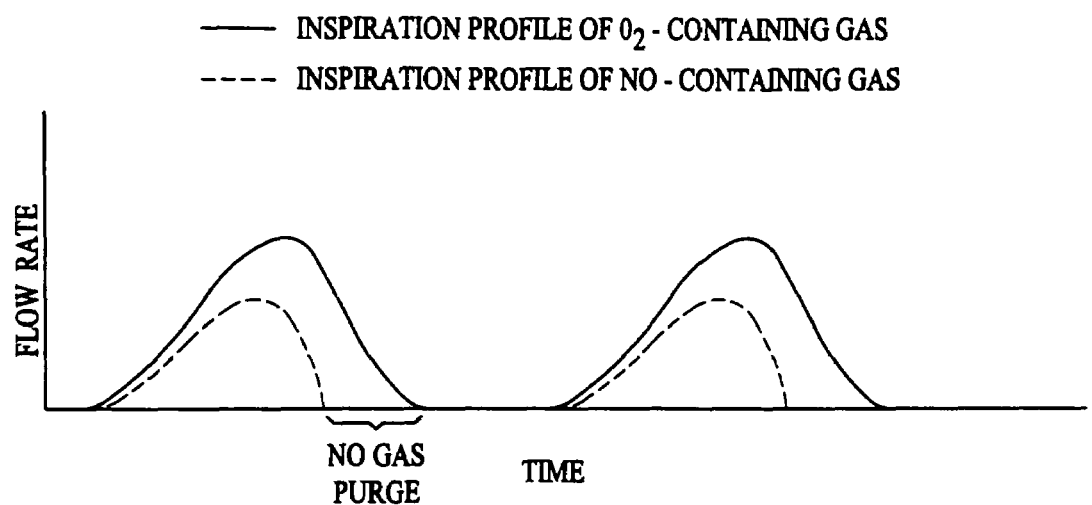
FIG. 3(a) illustrates the inspiration profile of the oxygen-containing gas and the NO-containing gas for delivering a non-constant concentration of NO to a patient, wherein the concentration of NO is higher at the beginning of inspiration than at the end of inspiration.
Figure 3B:
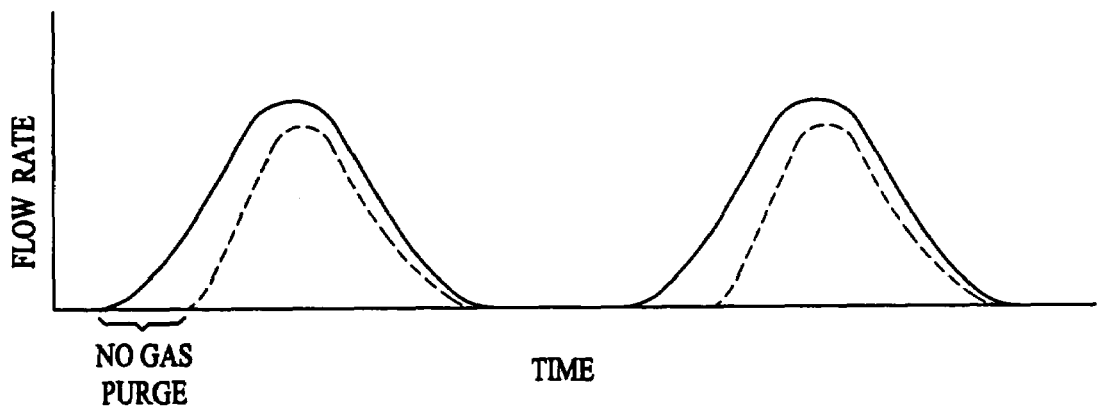
FIG. 3(b) illustrates the inspiration profiles of the oxygen-containing gas and the NO-containing gas for delivering a non-constant concentration of NO to a patient, wherein the concentration of NO is higher at the end of inspiration than at the beginning of inspiration.

As an alternative embodiment, the CPU 36 controls the flow of the NO-containing gas 22 and the oxygen-containing gas 20 to provide for a non-constant concentration of NO in the breathing gas of a patient 4. FIGS. 3(a) & 3(b) show the flow profiles of the operation of the device 2 according to this embodiment.

FIG. 3(a) shows a variable concentration delivery mode for NO that provides a higher concentration of NO to the patient 4 during the beginning of inspiration. As seen in FIG. 3(a), the flow profile of the NO-containing gas 22 is less than the flow profile of the oxygen-containing gas 20. In addition, the flow profile of the NO-containing gas 22 closely tracks the oxygen-containing gas 20 flow profile at the beginning of inspiration (quasi-proportional), but begins to tail-off as inspiration progresses. In this manner, the difference between the flow profiles of the oxygen-containing gas 20 and the NO-containing gas 22 progressively increases through the remainder of inspiration. In this method of delivery, a higher concentration of NO is delivered to the patient 4 at the beginning of inspiration than at the end of inspiration. This flow profile is used when it is desirous for NO to be delivered deep within the lungs, for instance, to treat pulmonary hypertension. Unlike the NO delivery method of the '433 patent that delivers a discrete bolus or short plug of NO, the present method provides a gradual gradient of NO in the lungs wherein the concentration of NO in the upper airway is lower than the concentration of NO in the lowermost regions of the lung. In addition, the flow profile of the NO-containing gas 22 more closely matches the flow profile of the oxygen-containing gas 20. The flow profile of the NO-containing gas 22 is not a square wave as disclosed in the '433 patent. Rather, the flow profile is quasi-proportional to the oxygen-containing gas 20 profile.

Figure 3:
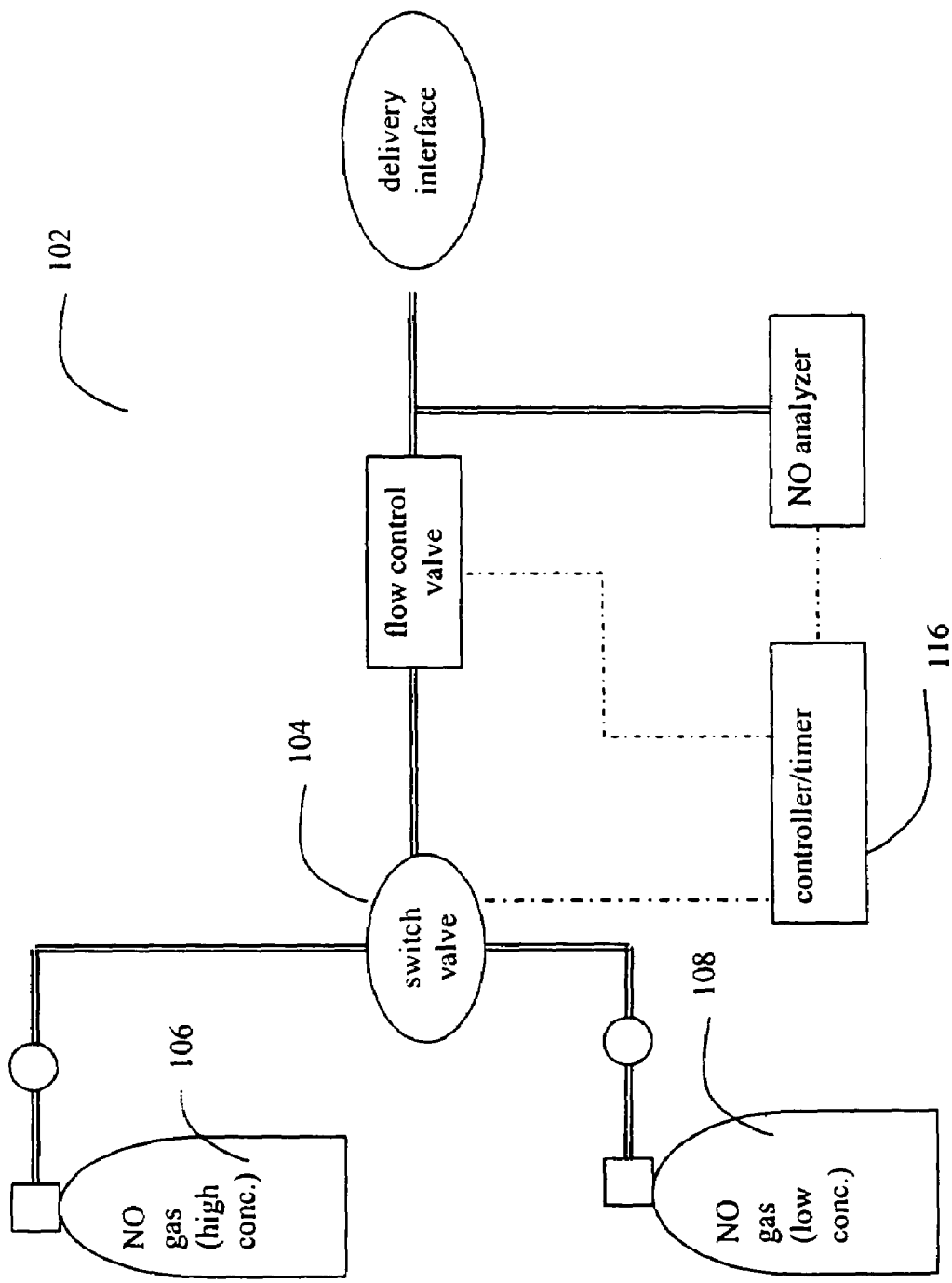

This method is advantageous over the method of delivery disclosed in the '433 patent because the bolus delivered in the '433 patent is of such a short length that the targeted area of the lung can be missed entirely. By having a continuous tapering of NO concentration, it is assured that the target area of the lungs is bathed in at least some concentration of NO. Moreover, since the difference between the flow rate of the oxygen-containing gas 20 and the NO-containing gas 22 increases (or decreases as shown in FIG. 3(*b*)) during the time of inspiration, the total amount of NO delivered per breath is smaller when compared to a square wave profile of NO. The pressurized cylinder 24 containing the NO-containing gas 22 thus needs less frequent changing. Another important aspect of this method of delivery is that the flow profile of the NO-containing gas 22 reaches zero prior to the flow profile of the oxygen-containing gas 20. See FIGS. 3(*a*) and 3(*b*). The oxygen-containing gas 20 that continues to flow aids in purging the inspiration limb 8 of NO.

With respect to the flow profile shown in FIG. 3(*a*), and as stated previously, the difference between the flow profiles of the oxygen-containing gas 20 and the NO-containing gas 22 progressively increases through the remainder of inspiration. The rate of this increase, however, may be controlled by the CPU 36. For example, the increase may be linear, non-linear, exponential, etc., depending on the desired flow profile of the NO-containing gas 22. Further, the rate of this increase may be set by the input device 42.

Referring now to FIG. 3(*b*), another flow profile is shown for the NO-containing gas 22 that provides for a greater NO concentration at the end of the patient's 4 inspiration profile.

As seen in FIG. 3(*b*), the flow profile of the NO-containing gas 22 is less than the flow profile of the oxygen-containing gas 20. In addition, the flow profile of the NO-containing gas 22 is substantially less than the oxygen-containing gas 20 at the beginning of inspiration. Preferably, the flow rate of the NO-containing gas 22 is zero at the beginning of inspiration, while the flow rate of the oxygen-containing gas 20 is positive. In addition, as inspiration proceeds, the difference between the flow profile of the oxygen-containing gas 20 and the NO-containing gas 22 progressively decreases. In this profile, a higher concentration of NO is delivered to the upper airway region of the lungs. This method is used, for example, in breathing diseases relating to broncho-constriction of the airways, such as asthma.

With respect to the flow profile shown in FIG. 3(*b*), the difference between the flow profiles of the oxygen-containing gas 20 and the NO-containing gas 22 progressively decreases through the remainder of inspiration. The rate of this decrease, however, may be controlled by the CPU 36. For example, the decrease may be linear, non-linear, exponential, etc., depending on the desired flow profile of the NO-containing gas 22. Further, the rate of this decrease may be set by the input device 42.

With respect to the purge feature of this method, at the beginning of the inspiration profile, the oxygen-containing gas 20 is flowing, but the NO-containing gas 22 is not. Consequently, the flow of the oxygen-containing gas 20 acts to purge the inspiration limb 8 of NO that may have remained from the previous breath.

Figure 4A:
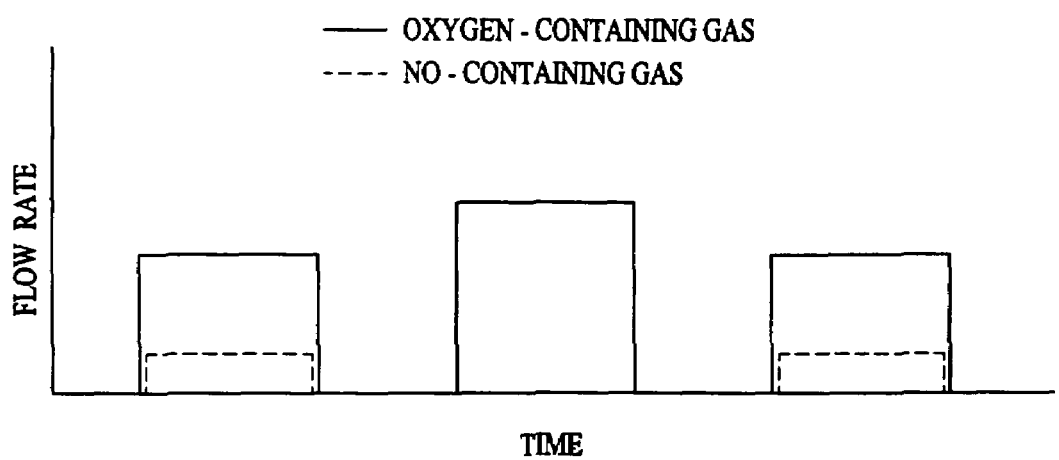
FIG. 4(a) is a flow profile of oxygen-containing gas and NO-containing gas where enriched-oxygen is delivered between breaths.
Figure 4B:
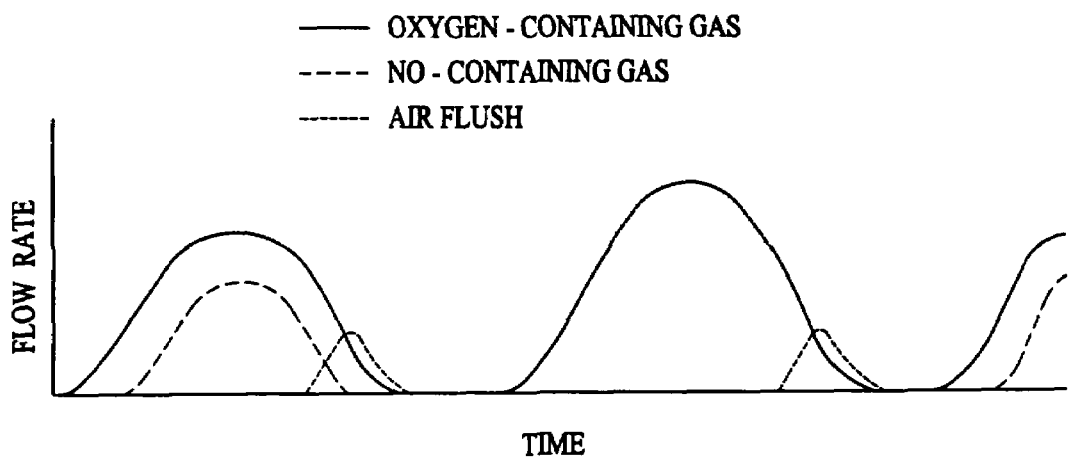
FIG. 4(b) shows the flow profile of the oxygen-containing gas, the NO-containing gas, and the air flush according to one aspect of the invention.

In another flow profile, shown in FIG. 4(*a*), a patient 4 receives a first inhalation containing both oxygen-containing gas 20 and NO-containing gas 22. In the next inhalation breath, the patient receives just oxygen-containing gas 20. Preferably, this inspiration contains a relatively high concentration of oxygen-containing gas 20 (oxygen-enriched). In the third inspiration, the patient 4 again receives an oxygen-containing gas 20 and an NO-containing gas 22. While the flow profile shown in FIG. 4(*a*) is shown as alternating between oxygen-containing gas-only 20 and NO-containing gas 22 plus oxygen-containing gas 20, the profile could also include, for example, two or more oxygen-containing gas 22-only inspirations between inspirations having both oxygen-containing gas 20 and NO-containing gas 22.

Yet another flow profile is shown in FIG. 4(*b*). In FIG. 4(*b*), a patient 4 is delivered, on inspiration, a flow profile including an oxygen-containing gas 20 and a NO-containing gas 22. At or near the end of this inspiration, an air flush is delivered to the patient 4. The air flush serves to remove any NO-containing gas 22 that may be in the inspiration limb 8.

In the next inspiration, an oxygen-containing gas 20 is delivered to the patient 4 without any NO-containing gas 22. Preferably, the oxygen-containing gas 20 includes an elevated level of oxygen (enriched-oxygen). At or near the end of this inhalation, another air flush is delivered to the patient 4. This air flush is delivered to the patient 4 and serves to remove any enriched-oxygen remaining in the inspiration limb 8 as well as any residual NO gas.

Figure 5:
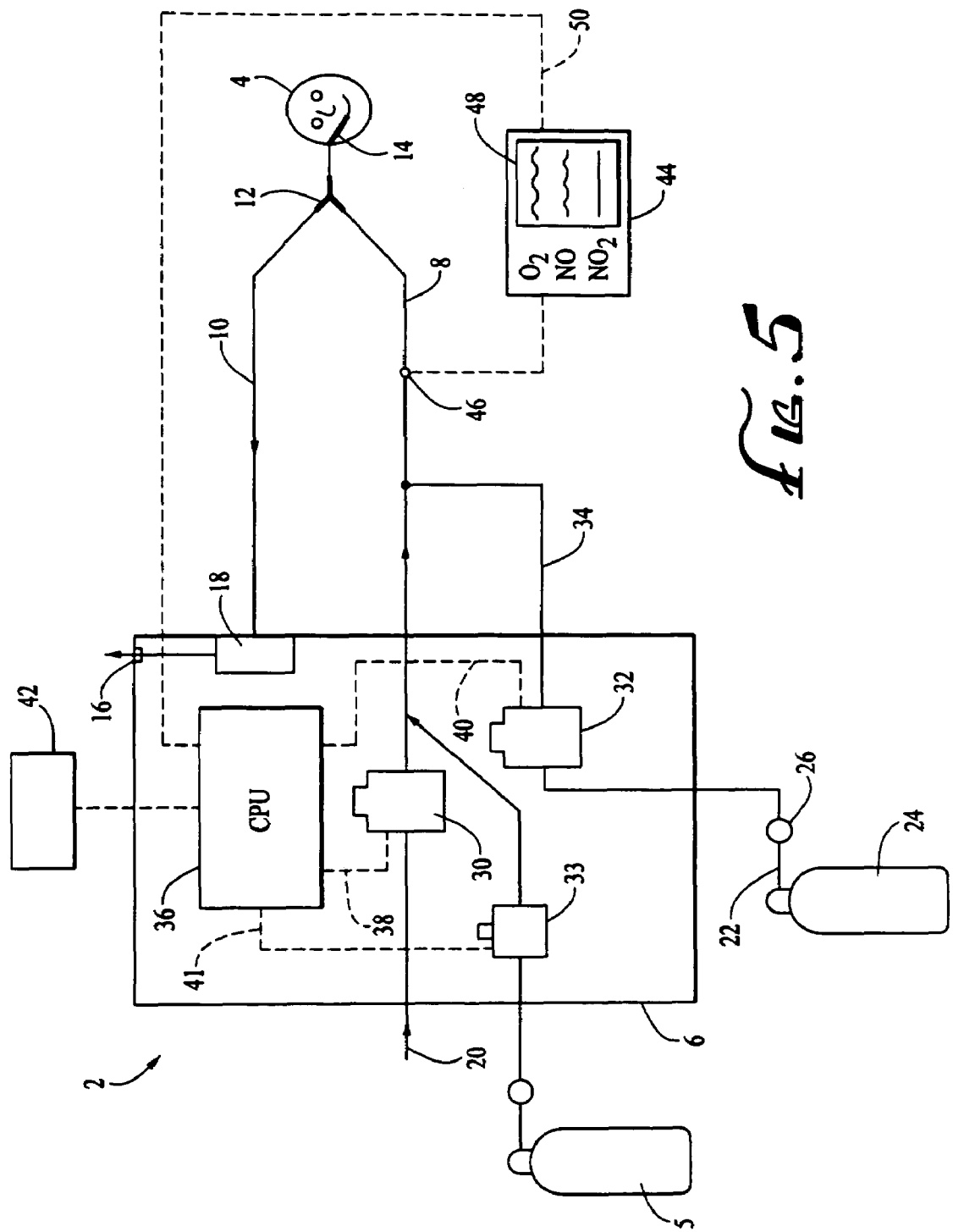
FIG. 5 is a schematic illustration of a device being used with a patient supported by mechanical ventilation wherein the air flush aspect is utilized.

In this embodiment, there are two separate sources of oxygen-containing gas 20. One source is the air used to flush the inspiration limb 8 while the other source is the enriched-oxygen-containing gas 20. The source of air for the air flush can be, for example, a separate pressurized cylinder, wall supply, compressor, pump, or the like. FIG. 5, for example, shows the air being stored in a pressurized cylinder 25 while the enriched oxygen-containing gas 20 enters the device via a wall supply or the like. The flow of air is modulated by a third control valve 33 that is controlled by the CPU 36 via signal line 41.

It should be noted that by controlling the flow rates of the oxygen-containing gas 20 and the NO-containing gas 22 via a single CPU 36, the device 2 can use a pressurized cylinder 24 having a relatively high concentration of NO (about 1000 ppm), since the second flow controller 32 is always controlled to provide a smaller flow rate of NO-containing gas 22 than the flow rate of the oxygen-containing gas 20.

The device 2 can further include an optional gas monitor 44. The gas monitor 44 preferably monitors the concentration of one or more of the following gases in the inspiration limb 8 of the device 2: oxygen, NO, and $NO_2$. The gas monitor 44 determines the concentration of gas(es) via a sensor(s) 46 located in the inspiration limb 8. The sensor(s) 46 can be a chemilluminesence-type, electrochemical cell-type, or spectrophotometric-type sensor 46 based on the accuracy and response time desired. The gas monitor 44 preferably includes a display screen 48 that illustrates, on a real-time basis or as close to a real-time basis as possible, the concentrations of the measured gases. The gas monitor 44 preferably reports the gas concentration data to the CPU 36 via signal line 50.

As an optional safety feature of the device 2, the CPU 36 can use the real-time concentration data to determine if the NO or $NO_2$ concentration levels exceed certain predetermined set-points input via input device 42. For example, if the $NO_2$ concentration exceeds the set-point concentration, the CPU can send a close-valve signal to the second control valve 32. In this regard, the NO-containing gas 22 is shut-off entirely.

In addition, the level of oxygen in the gas stream can also be monitored via the monitor 44. If the oxygen concentration drops below a certain concentration, the CPU 36 can decrease the flow of the NO-containing gas 22 and/or increase the flow rate of the oxygen-containing gas 20.

It should be noted that the above-described device 2 can also be used in modes other than continuous mandatory ventilation. For example, the device 2 can also be used with assisted ventilation, synchronized intermittent ventilation (SIMV), intermittent mandatory ventilation (IMV), and pressure support ventilation. Still other modes of operation will also work with the device 2.

Figure 6:
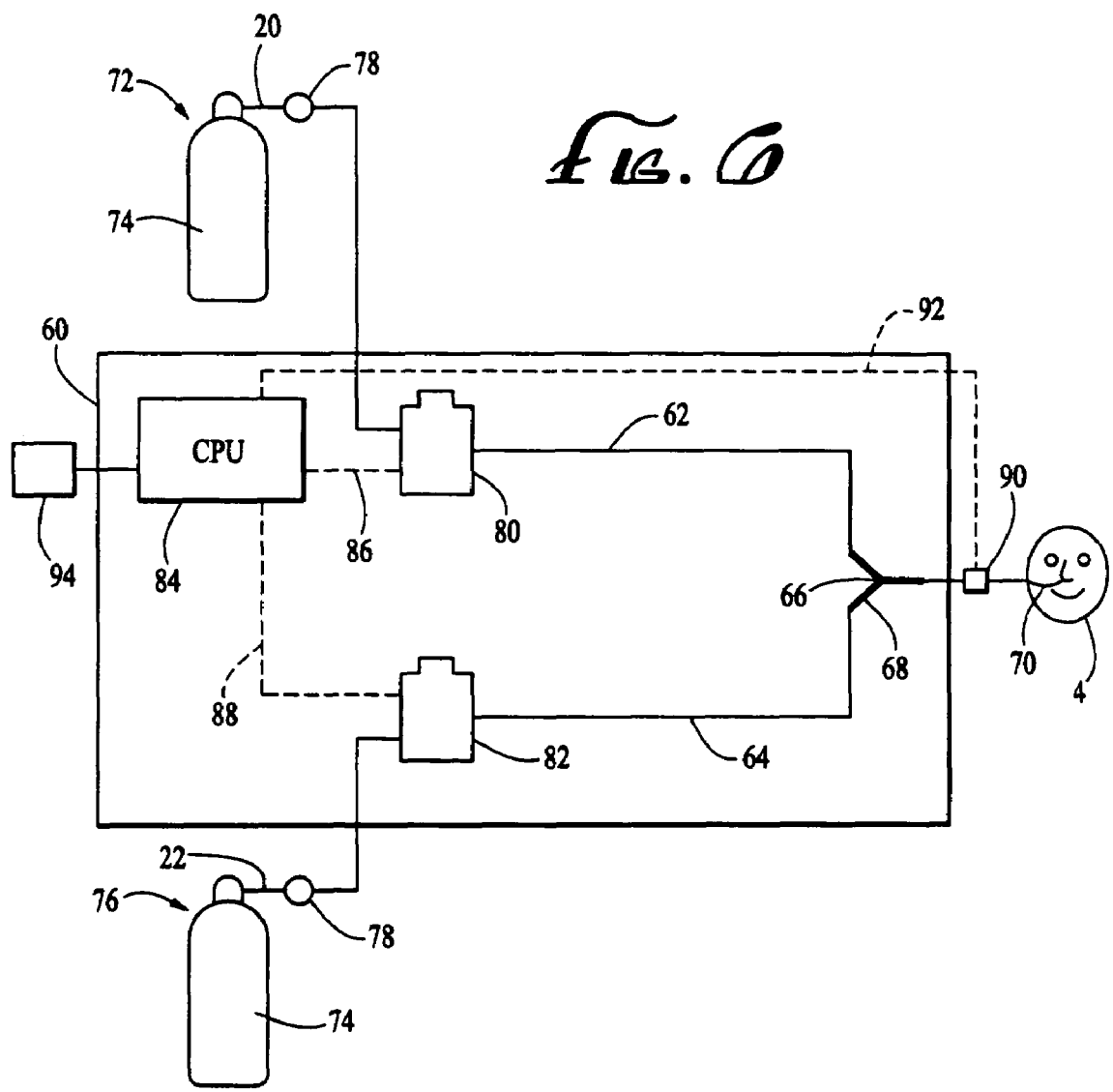
FIG. 6 is a schematic illustration of the device being used with a spontaneously breathing patient.

In another separate aspect of the invention, as shown in FIG. 6, a device 60 for a spontaneously breathing patient 4 is disclosed. The device 60 includes an oxygen-containing gas limb 62 and a NO-containing gas limb 64. Both the oxygen-containing gas limb 62 and a NO-containing gas limb 64 are preferably made of a hollow, flexible tubing material. The oxygen and NO limbs 62, 64 combine at a mixing point 66. The mixing point 66 may include a Y-piece 68 that connects with another hollow flexible tube that then travels to the patient 4. The combined gases enter the patient's airway via delivery means. The delivery means preferably includes a patient inspiration interface device 70. By way of illustration and not by way of limitation, the patient inspiration interface device 70 can include a tube for intubation into the patient's 4 airway, a nasal cannula, a face mask, or transtracheal catheter.

A source 72 of oxygen-containing gas 20 delivers the oxygen-containing gas 20 into the oxygen-containing gas limb 62. The source 72 of oxygen-containing gas 20 preferably is a pressurized cylinder 74. The pressurized cylinder 74 can contain atmospheric air, compressed air, compressed air mixed with oxygen, or a mixture of oxygen and nitrogen. The main requirement for the oxygen source 72 is that the gas contain at least some component of oxygen.

While the pressurized cylinder 74 is the preferable method of storing the oxygen source 72, other storage means such as a dedicated feed line (wall supply), can also be used. Alternatively, the oxygen can be delivered from a compressor or pump.

The NO source 76 is shown as a pressurized cylinder 74. While the use of a pressurized cylinder 74 is the preferable method of storing the NO-containing gas 22, other storage and delivery means, such as a dedicated feed line, can also be used. Preferably, the NO-containing gas 22 is a mixture of $N_2$ and NO. While $N_2$ is typically used to dilute the concentration of NO, any inert gas can also be used. When the NO-containing gas 22 is stored in pressurized cylinder 74, it is preferable that the concentration of NO in the cylinder fall within the range of about 800 ppm to about 1200 ppm.

As with the inspiration concentration of NO gas in the mechanical ventilator embodiment, it is generally preferable that the NO concentration fall with the range of about 1 ppm to about 100 ppm. In the spontaneous-breathing embodiment, it is preferable to use a NO source 76 at higher concentrations for the same stated reasons for the mechanical ventilator embodiment.

When pressurized cylinders 74 are used to store the oxygen and NO-containing gases 20, 22, pressure regulators 78 are preferably used to reduce the pressures of the respective gases.

The device 60 includes a first control valve 80 that is located in-line between the source 72 of oxygen-containing gas 20 and the oxygen-containing gas limb 62. As with the mechanical ventilator device 2, The first control valve 80 thus receives the oxygen-containing gas 20 at an input port and modulates, or controls the flow of the oxygen-containing gas 20 into the oxygen-containing gas limb 62 through a second export port. The first control valve 80 can include, for example, a proportional control valve that opens (or closes) in a progressively increasing (or decreasing if closing) manner depending on an electronic input. As another example, the first control valve 80 can also include a mass flow controller. The first control valve 80 can include any number of control valves that can quickly and accurately alter the flow rate of a gas across a relatively wide range of flow rates.

Figure 7A:
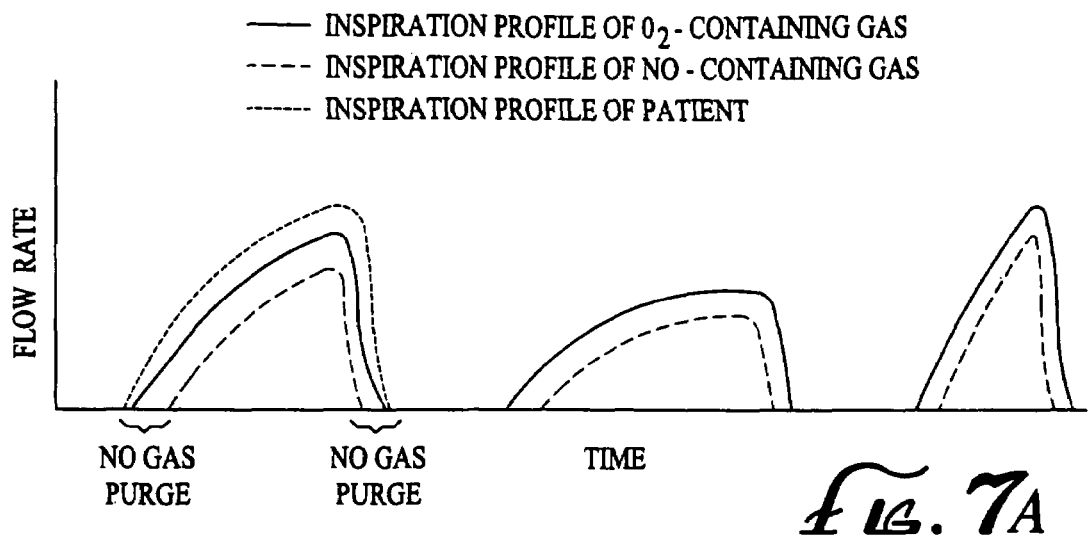
FIG. 7(a) illustrates a inspiration profile for a spontaneously breathing patient in addition to the flow profiles of the oxygen-containing gas and the NO-containing gas for delivering a constant concentration of NO to a patient.
Figure 7B:
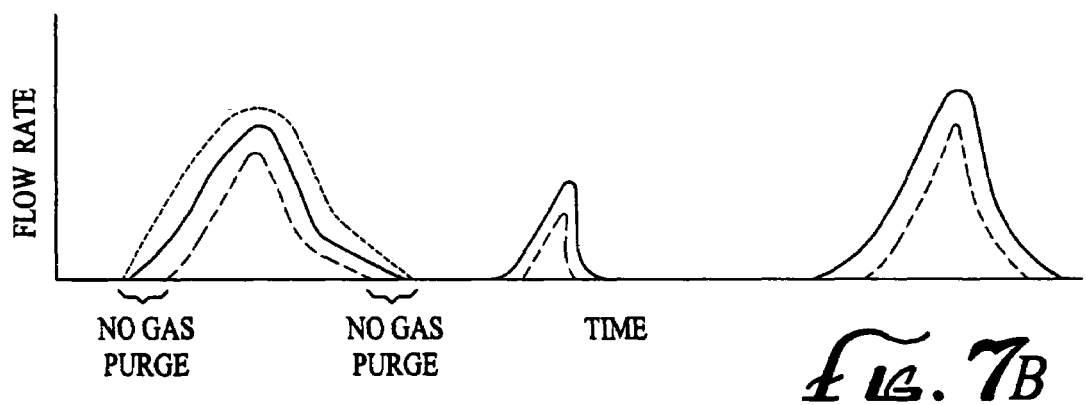
FIG. 7(b) illustrates another inspiration profile for a spontaneously breathing patient in addition to the flow profiles of the oxygen-containing gas and the NO-containing gas for delivering a constant concentration of NO to a patient.

The output of the first control valve 80 leads to the oxygen-containing gas limb 62 of the patient 4. In this regard, the first control valve 80 controls the inspiration profile of the oxygen-containing gas 20. The inspiration profile of the oxygen-containing gas 20 is the flow rate of the oxygen-containing gas 20 as a function of inspiration time. The inspiration profile of the oxygen-containing gas 20 can be seen in FIGS. 7(a) and 7(b).

Still referring to FIG. 6, a second control valve 82 is located in-line between the NO-containing gas 22 and the NO-containing gas limb 64. The second control valve 82 thus receives the NO-containing gas 22 at an input port and modulates, or controls the flow of the NO-containing gas 22 into the NO-containing gas limb 64 through a second export port. The second control valve 82 can include, for example, a proportional control valve that opens (or closes) in a progressively increasing (or decreasing if closing) manner depending on an electronic input. As another example, the second control valve 82 can also include a mass flow controller. The second control valve 82 can include any number of control valves that can quickly and accurately alter the flow rate of a gas across a relatively wide range of flow rates. Like the first control valve 80, the inspiration profile of the second control valve 82 controls the inspiration profile of the NO-containing gas 22. The inspiration profile of the NO-containing gas 22 is the flow rate of the NO-containing gas 22 as a function of time.

The spontaneously breathing device 60 includes a CPU 84. The CPU 84 controls the first and second control valves 80, 82. The CPU 84 sends, via signal lines 86, 88, signals to control the opening and closing of the control valves 80, 82.

The device 60 further includes an inspiration flow profile sensor 90 that is positioned in the patient 4 breathing limb. Preferably, the inspiration flow profile sensor 90 is located downstream of the mixing point 66, but upstream of the patient inspiration interface device 70. In one aspect, the inspiration flow profile sensor 90 detects the flow rate of the inspired gas by the patient 4. The inspiration flow profile sensor 90 thus detects the onset of inspiration as well as the inspiration flow profile throughout the remainder of the breath. The flow profile sensor 90 can include any number of devices, including venturi-based sensor, hot wire anemometer, rotating vane, thermal flow, pressure transducer, and the like. Preferably, a flow profile sensor 90 is used that can rapidly detect small changes in the breathing flow rate over a wide range of flow rates.

In another aspect, the flow profile sensor 90 detects only the onset of inspiration by the patient 4.

The inspiration profile sensor 90 reports the inspiration flow rate data back to the CPU 84 via signal line 92 on preferably a real-time basis (or as close to a real-time basis as possible). The flow rate data reported back to the CPU 84 is the flow rate of the breathing gas (oxygen-containing gas 20 and NO-containing gas 22) as a function of time. This data represents the inspiration flow profile for each individual breath.

As an alternative to measuring the flow rate of the breathing gas as a function of time, the inspiration profile sensor 90 can just measure the onset of inspiration. The data reflecting the onset of inspiration is delivered as a signal to CPU 84. Pre-programmed flow profiles of the oxygen-containing gas 20 and the NO-containing gas 22 are then delivered to the patient 4. In general, the pre-programmed flow profiles of the oxygen-containing gas 20 and the NO-containing gas 22 are determined by empirical studies of patient inhalation characteristics. The flow profile of the oxygen-containing gas 20 and the NO-containing gas 22 can be proportional, quasi-proportional, or any other pre-determined flow pattern. This aspect is shown, for example, in FIG. 7(*c*).

Figure 7C:
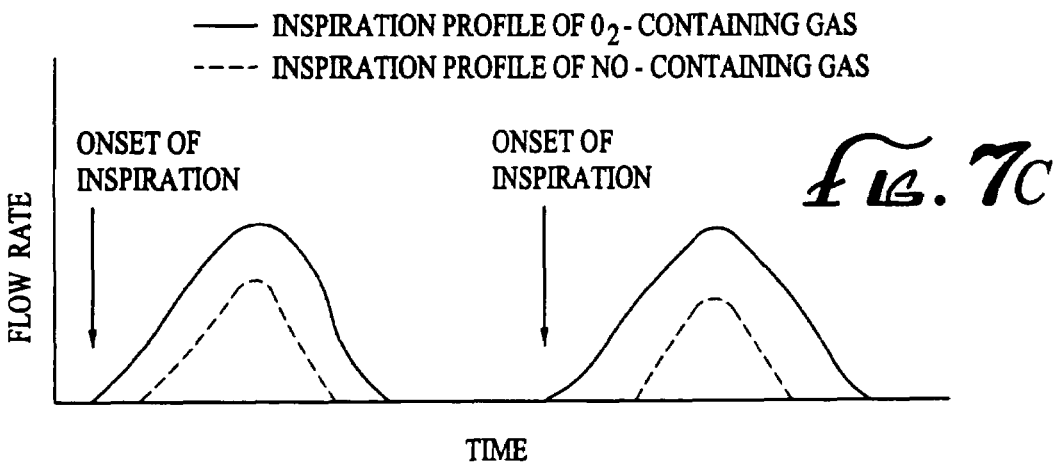
FIG. 7(c) illustrates pre-programmed inspiration profiles of the oxygen-containing gas and the NO-containing gas.

Based on the signal received from the inspiration profile sensor 90, the CPU 84 controls both the first and second control valves 80, 82 to delivery respective flow profiles of oxygen and NO. In one aspect of the invention, the CPU 84 contains instructions to deliver proportional flows of both the oxygen-containing gas 20 and the NO-containing gas 22. In this regard, a steady concentration of NO is delivered to the patient. This flow pattern is embodied in FIGS. 7(*a*) & 7(*b*). The dotted-line in FIG. 1 illustrates the inspiration flow profile of the patient 4. As can be seen in FIGS. 7(*a*) & 7(*b*), not only is the flow of the oxygen-containing gas 20 proportional to the inspirational flow of the patient 4, the flow of the NO-containing gas 22 is proportional to both the inspirational flow of the patient 4 as well as the inspirational flow of the oxygen-containing gas 20.

The device 60 preferably includes an input device 94. The input device 94 can be any number of devices including, for example, a computer, diskette, control panel, and the like. The input device 94 can control, for example, the set-point concentration of NO in the breathing gas. The input device 94 can thus alter the degree of proportionality between the flow profile of the oxygen-containing gas 20 and the flow profile of the NO-containing gas 22. A higher degree of proportionality (i.e., the flow profile of the NO-containing gas 22 more closely tracks the flow profile of the oxygen-containing gas 20) would generally produce a higher concentration of inspired NO. The degree of proportionality also affects the timing of the NO gas purge.

The input device 94 may also input gas purge parameters to the CPU 84 to determine when the flow profile of the NO-containing gas 22 is truncated. This can be done, for example, by establishing a time after inspiration is started at which the flow profile of the NO-containing gas 22 is dropped to zero. Alternatively, the NO-containing gas 22 can terminate once the flow rate of the oxygen-containing gas 20 drops below a certain pre-set level. These settings can be input to the CPU 84 via the input device 94.

Still referring to FIGS. 7(*a*) & 7(*b*), the proportional flow of the NO-containing gas 22 also provides the device 60 and method with a purge feature to purge any NO gas from the lines and the patient inspiration interface device 70. At both the beginning and end of the patient's 4 inspiration, there is a positive flow of the oxygen-containing gas 20, while the flow of the NO-containing gas 22 is zero. Consequently, at the beginning and end of each breath, the device is purged on NO gas.

With respect to the spontaneous-breathing embodiment, the present invention also contemplates using a CPU 84 that gives the device 60 complete programmability. In this regard, the flow profiles of the both the oxygen-containing gas 20 and the NO-containing gas 22 can be controlled during a single breath. While proportional and quasi-proportional flow profiles are disclosed in greater detail herein, it should be appreciated that any flow profile (of the oxygen-containing gas 20 or the NO-containing gas 22) can be produced for a single breath of a patient 4. Complete programmability is also possible where the device employs input device 94.

While CPU 84 is shown as the preferred controller for controlling the flow profiles of the oxygen-containing gas 20 and the NO-containing gas 22, the present invention further contemplates using an analog switching mechanism (not shown) as an alternative controller.

The device 60 can further include an optional gas monitor 96. The gas monitor 96 preferably monitors the concentration of one or more of the following gases in the inspiration limb of the device 60: oxygen, NO, and $NO_2$. The gas monitor 96 determines the concentration of gas(es) via a sensor(s) 98 located in the inspiration limb. The sensor(s) 98 can be a chemilluminesence-type, electrochemical cell-type, or spectrophotometric-type sensor 98 based on the accuracy and response time desired. The gas monitor 96 preferably includes a display screen 100 that illustrates, on a real-time basis or as close to a real-time basis as possible, the concentrations of the measured gases.

Figure 8A:
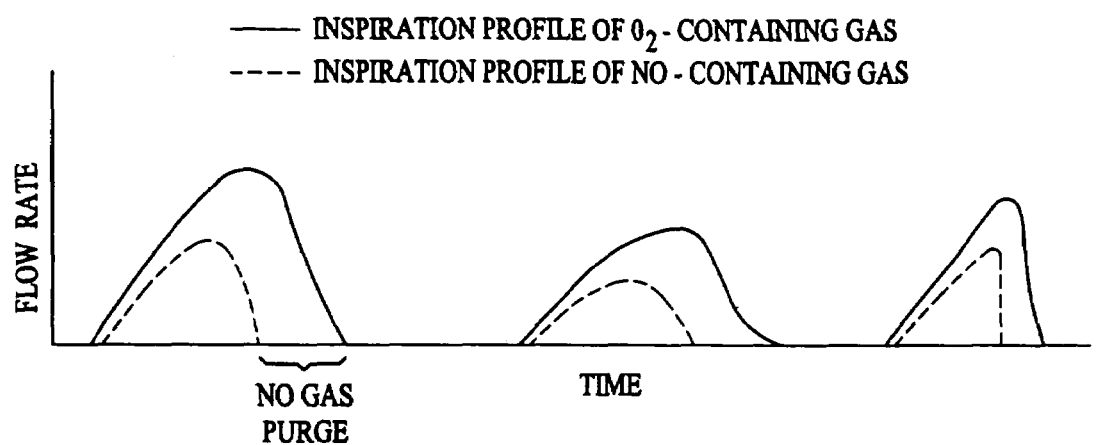
FIG. 8(a) illustrates an inspiration profile for the oxygen-containing gas and the NO-containing gas for delivering a non-constant concentration of NO to a patient, wherein the concentration of NO is higher at the beginning of inspiration than at the end of inspiration.

Referring now to FIG. 8(*a*), a separate aspect of the spontaneous-breathing device 60 will now be disclosed. In this aspect of the invention, a non-constant concentration of NO is delivered to the patient 4. In one aspect, the flow profile of the NO-containing gas 22 is such that a higher concentration of NO is delivered at the beginning of inspiration than the concentration delivered near the end of inspiration. In this aspect, the flow profile of the NO-containing gas 22 is less than flow profile of the oxygen-containing gas 20 and closely tracks the oxygen-containing gas 20 flow profile at the beginning of inspiration (quasi-proportional), but begins to tail-off as inspiration progresses. In this manner, the difference between the flow profiles of the oxygen-containing gas 20 and the NO-containing gas 22 progressively increases through the remainder of inspiration. This flow profile is used when it is desirous for NO to be delivered deep within the lungs, for instance, to treat pulmonary hypertension. This method of delivery, as stated previously, provides a gradual gradient of NO through the in the lungs rather than a bolus of NO that is disclosed in the '433 patent.

With respect to the flow profile shown in FIG. 8(*a*), and as stated previously, the difference between the flow profiles of the oxygen-containing gas 20 and the NO-containing gas 22 progressively increases through the remainder of inspiration. The rate of this increase, however, may be controlled by the CPU 84. For example, the increase may be linear, non-linear, exponential, etc., depending on the desired flow profile of the NO-containing gas 22. Further, the rate of this increase may be set by the input device 94.

This delivery method also contains gas purge feature that purges any NO gas from the lines and the patient inspiration interface device 70. At the end of the patient's 4 inspiration, there is a positive flow of the oxygen-containing gas 20, while the flow of the NO-containing gas 22 is zero. At this point in the patient's inspiration, the flow of oxygen-containing gas 20 purges the system of NO gas.

Referring now to FIG. 8(*b*), another flow profile is shown for the NO-containing gas 22 that provides for a greater NO concentration at the end portion of a patient's 4 inspiration. In this flow profile, the flow profile of the NO-containing gas 22 is substantially less than the oxygen-containing gas 20 flow profile. Most preferably, the flow profile of the NO-containing gas 22 starts out at zero, while the flow profile of the oxygen-containing gas 20 is positive. The flow profile of the NO-containing gas 22 begins to more closely track the flow profile of the oxygen-containing gas 20, wherein the difference between the flow profile of the oxygen-containing gas 20 and the NO-containing gas 22 progressively decreases throughout the remainder of inspiration. In this flow profile, a higher concentration of NO is delivered to the upper airway region of the lungs. This method is used, as stated previously, in breathing diseases relating to broncho-construction of the airways, such as asthma.

Figure 8B:
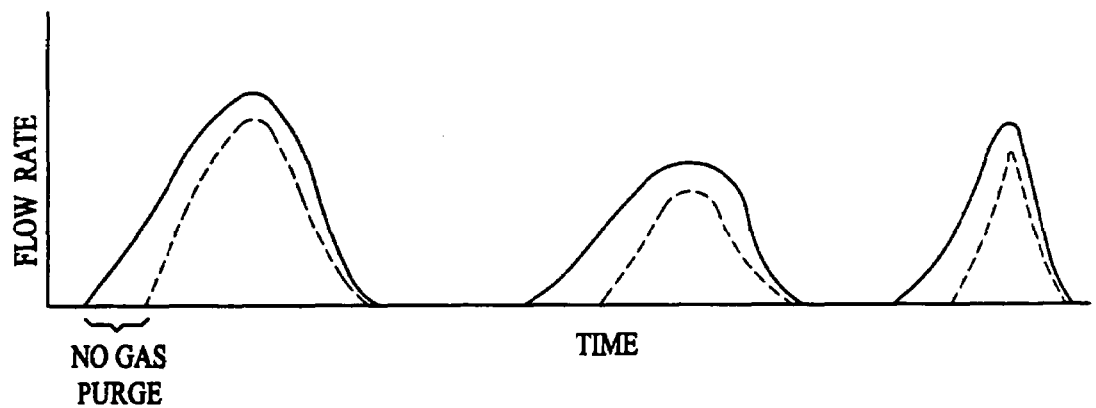
FIG. 8(b) illustrates another inspiration profile for the oxygen-containing gas and the NO-containing gas for delivering a non-constant concentration of NO to a patient, wherein the concentration of NO is higher at the end of inspiration than at the beginning of inspiration.

With respect to the flow profile shown in FIG. 8(b), the difference between the flow profiles of the oxygen-containing gas 20 and the NO-containing gas 22 progressively decreases through the remainder of inspiration. The rate of this decrease, however, may be controlled by the CPU 84. For example, the decrease may be linear, non-linear, exponential, etc., depending on the desired flow profile of the NO-containing gas 22. Further, the rate of this decrease may be set by the input device 94.

This delivery method also contains gas purge feature that purges any NO gas from the lines and the patient inspiration interface device 70. At the beginning of the patient's 4 inspiration, there is a positive flow of the oxygen-containing gas 20, while the flow of the NO-containing gas 22 is zero. At this point in the patient's inspiration, the flow of oxygen-containing gas 20 purges the system of NO gas. Consequently, any remaining NO that might have remained in the lines and/or patient inspiration interface device 70 from the previous breath are purged by the flow of the oxygen-containing gas 20.

Figure 9A:
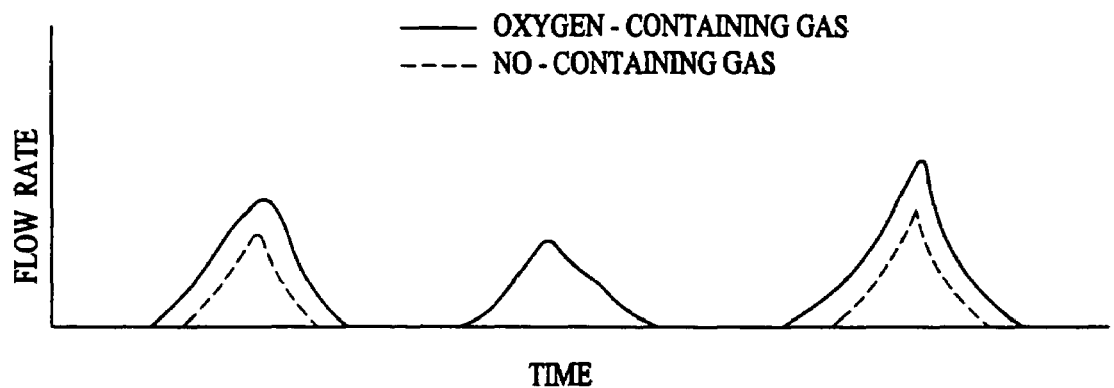
FIG. 9(a) is a flow profile of oxygen-containing gas and NO-containing gas where enriched-oxygen is delivered between breaths.

In another flow profile, shown in FIG. 9(a), a patient 4 receives a first inhalation containing both oxygen-containing gas 20 and NO-containing gas 22. In the next inhalation breath, the patient receives just oxygen-containing gas 20. Preferably, this inspiration contains a relatively high concentration of oxygen-containing gas 20 (oxygen-enriched). In the third inspiration, the patient 4 again receives an oxygen-containing gas 20 and an NO-containing gas 22. While the flow profile shown in FIG. 9(a) is show as alternating between oxygen-containing gas-only 20 and NO-containing gas 22 plus oxygen-containing gas 20, the profile could also include, for example, two or more oxygen-containing gas 22-only inspirations between inspirations having both oxygen-containing gas 20 and NO-containing gas 22.

Figure 9B:
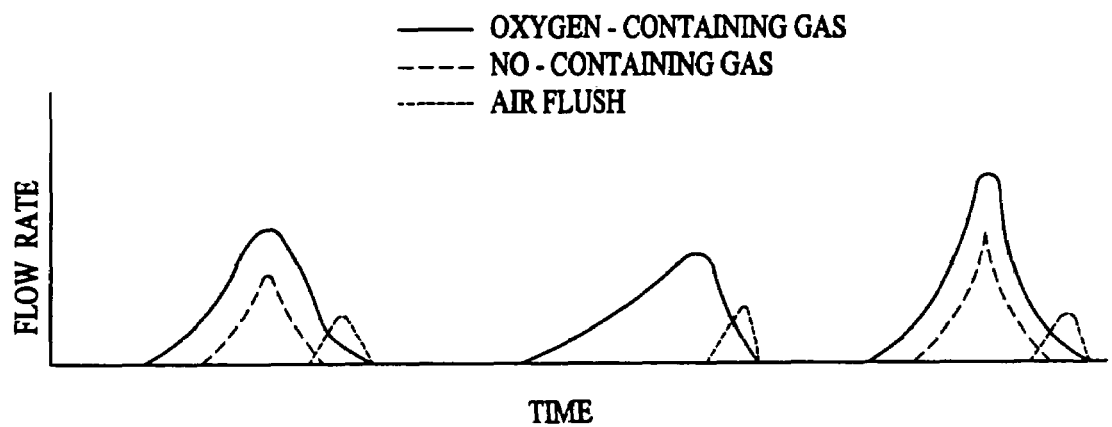
FIG. 9(b) shows the flow profile of the oxygen-containing gas, the NO-containing gas, and the air flush according to one aspect of the invention.

Yet another flow profile is shown in FIG. 9(b). In FIG. 9(b), a patient 4 is delivered, on inspiration, a flow profile including an oxygen-containing gas 20 and a NO-containing gas 22. At or near the end of this inspiration, an air flush is delivered to the patient 4. The air flush serves to remove any NO-containing gas 22 that may be in the inspiration limb 8.

In the next inspiration, an oxygen-containing gas 20 is delivered to the patient 4 without any NO-containing gas 22. Preferably, the oxygen-containing gas 20 includes an elevated level of oxygen (enriched-oxygen). At or near the end of this inhalation, another air flush is delivered to the patient 4. This air flush is delivered to the patient 4 and serves to remove any enriched-oxygen gas remaining in the inspiration limb 8.

Figure 10:
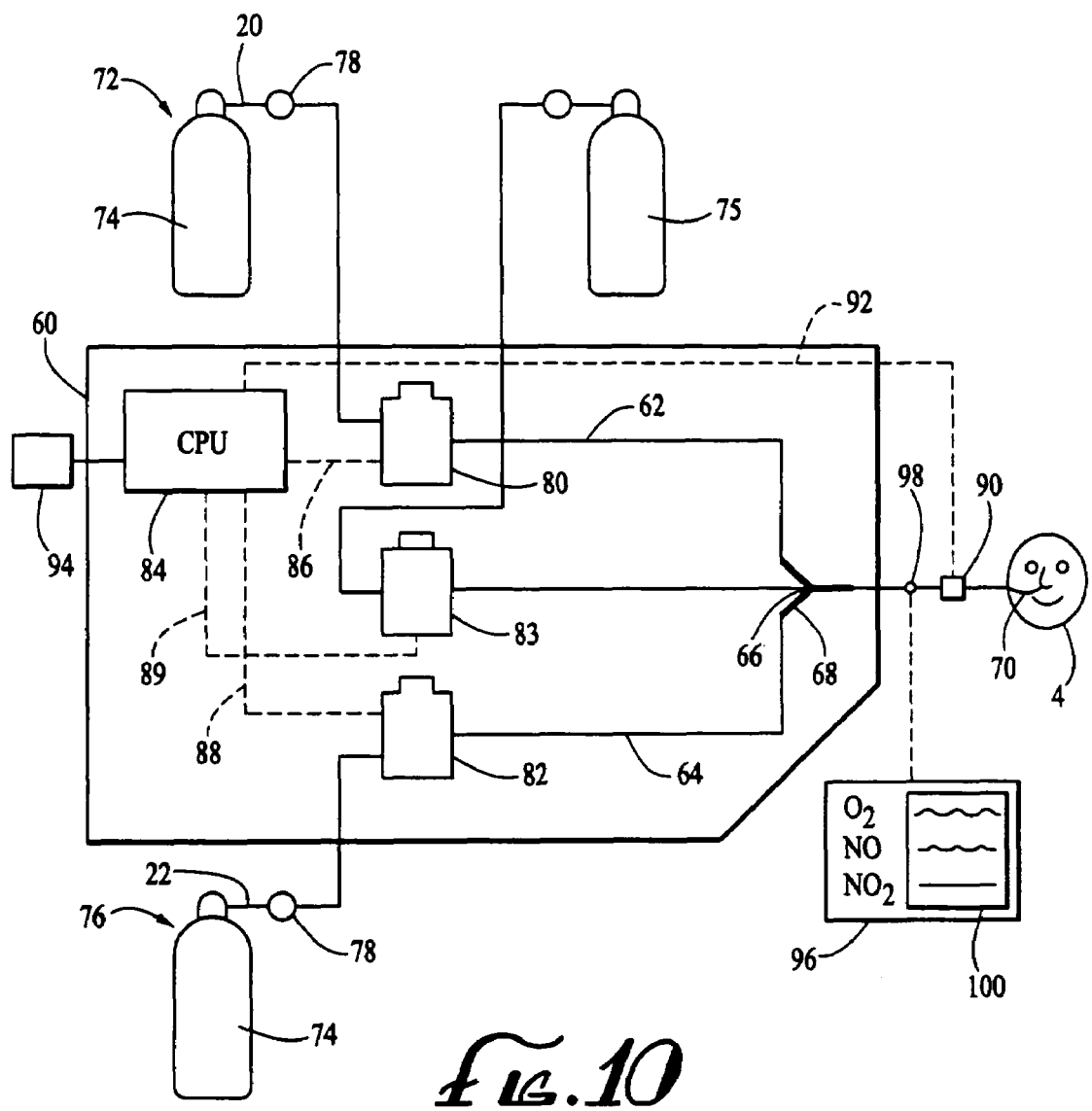
FIG. 10 is a schematic illustration of a device being used with a spontaneously-breathing patient wherein the air flush aspect is utilized.

In this embodiment, there are two separate sources of oxygen-containing gas 20. One source is the air used to flush the device 60 while the other source is the enriched-oxygen-containing gas 20. The source of air for the air flush can be, for example, a separate pressurized cylinder, wall supply, compressor, pump, or the like. FIG. 10, for example, shows the air being stored in a pressurized cylinder 75 while the enriched oxygen-containing gas 20 enters the device via a wall supply or the like. The flow of air is modulated by a third control valve 83 that is controlled by the CPU 84 via signal line 89.

Intermittent Dosing

It is currently believed that at higher concentration, nitric oxide gas overwhelms the defense mechanism of pathogens that use the mammalian body to replenish their thiol defense system. The thiol defense system may include for example, the mycothiol for mycobacterium or glutathione for other bacteria. Once this defense mechanism is depleted, the pathogen is defenseless against the killing effects of nitric oxide. A lower dose or concentration of nitric oxide gas delivered in between the bursts of high concentration nitric oxide maintains nitrosative stress pressure on the pathogens to prevent them from rebuilding their defense system to an adequate level. Thus, a preferred therapeutic or delivery profile for combating pathogens may comprise the delivery of a first concentration of nitric oxide gas for a number of time periods interspersed with intervals in between wherein a second concentration of nitric oxide is administered during the intervals.

The first concentration is preferably at a high concentration sufficient to kill or inhibit microbial growth. For example, the first concentration may range from about 80 ppm to 400 ppm, more preferably between 150 to 250 ppm and most preferably between 160 ppm to 200 ppm.

Figure 11:
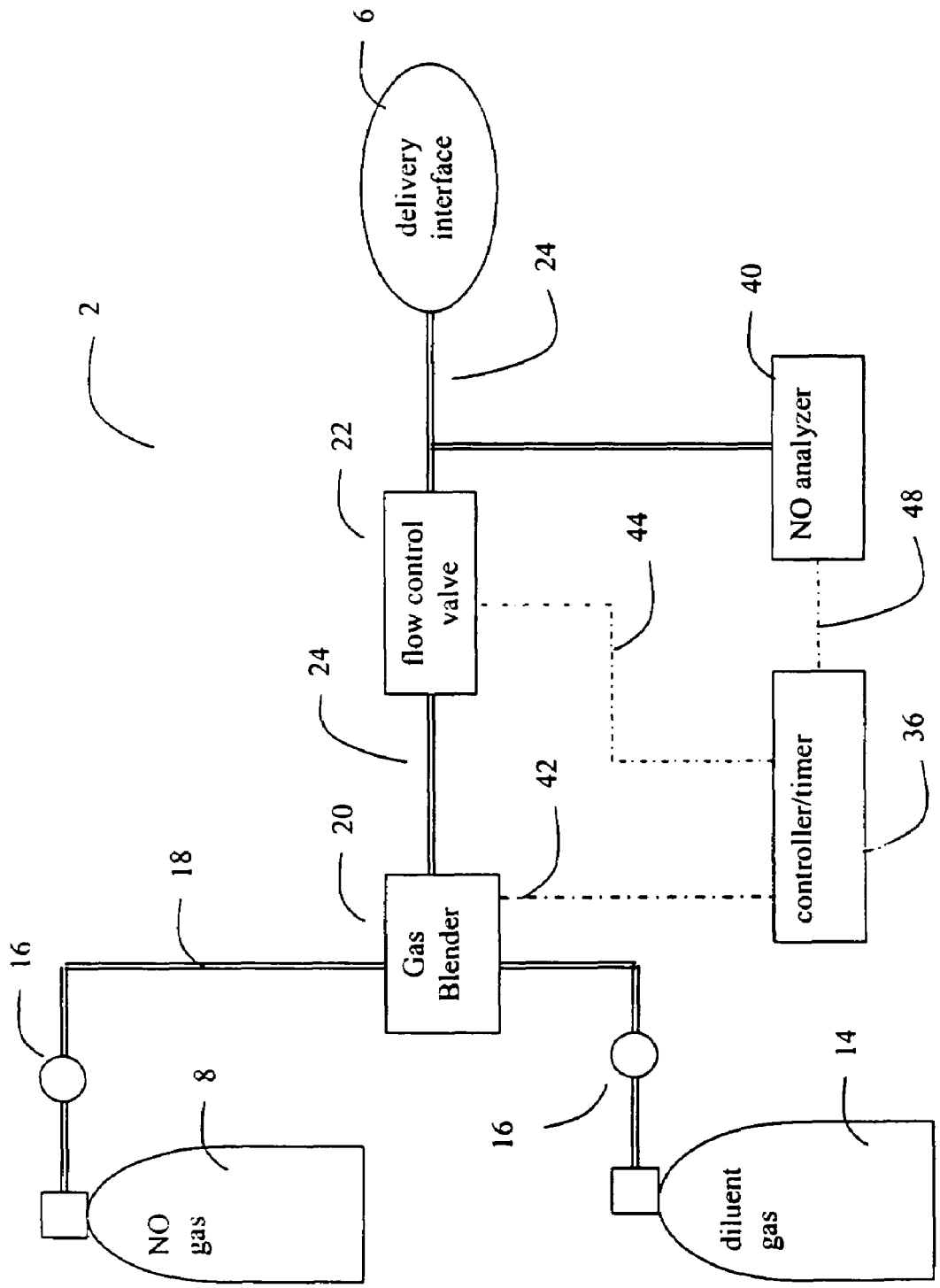
Figure 12:
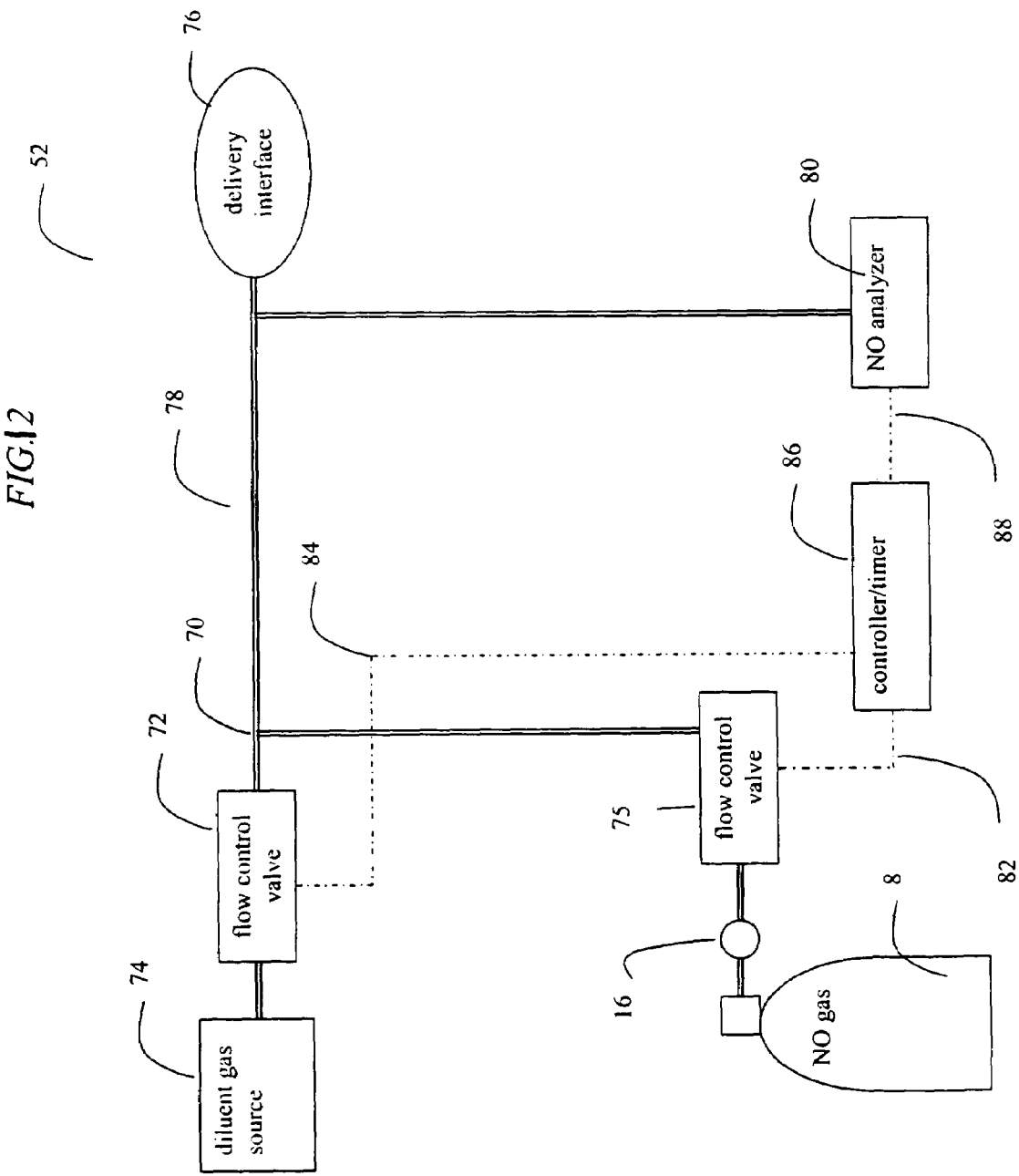

The second concentration is preferably at low concentration of nitric oxide gas such as ranging from 20 to 80 ppm. Alternatively, it should also be understood that the second concentration can also be zero ppm or close to trace amount of nitric oxide gas. Turning now to the figures, FIGS. 11-13 illustrate various embodiments of a nitric oxide delivery device for use with the present invention. FIG. 11 shows, in its most general sense, a NO delivery device 2 that includes a source of nitric oxide gas 8 adapted for delivery of the NO gas to a mammal through a delivery interface 6. FIG. 11 illustrates one preferred embodiment of the invention.

In FIG. 11, the NO gas source 8 is a pressurized cylinder containing NO gas. While the use of a pressurized cylinder is the preferred method of storing the NO-containing gas source 8, other storage and delivery means, such as a dedicated feed line (wall supply) can also be used. Typically, the NO gas source 8 is a mixture of N2 and NO. While N2 is typically used to dilute the concentration of NO within the pressurized cylinder, any inert gas can also be used. When the NO gas source 8 is stored in a pressurized cylinder, it is preferable that the concentration of NO in the pressurized cylinder fall within the range of about 800 ppm to about 10,000 ppm. Commercial nitric oxide manufacturers typically produce nitric oxide mixtures for medical use at around the 1000 ppm range. Pressurized cylinders containing low concentrations of NO (e.g., less than 100 ppm NO) can also be used in accordance with the device and method disclosed herein. Of course, the lower the concentration of NO used, the more often the pressurized cylinders will need replacement.

FIG. 12 also shows a source of diluent gas 14 as part of the NO delivery device 2 that is used to dilute the concentration of NO. The source of diluent gas 14 can contain N2, O2, Air, an inert gas, or a mixture of these gases. It is preferable to use a gas such as N2 or an inert gas to dilute the NO concentration at lower concentration since these gases will not oxidize the NO into NO2 as would $O_2$ or air. Nevertheless, for inhalation applications for delivery of high concentration of NO where higher concentration of nitrogen may already be present, the NO flow may be supplemented or diluted with oxygen to prevent the displacement of oxygen by nitrogen that may lead to asphyxiation. It is preferred, especially when delivering higher concentration of NO gas that delivery line downstream of the injection site or gas blender be minimized to reduce the risk of formation of NO2. The source of diluent gas 14 is shown as being stored within a pressurized cylinder. While the use of a pressurized cylinder is shown in FIG. 11 as the means for storing the source of diluent gas 14, other storage and delivery means, such as a dedicated feed line (wall supply) can also be used. The source of diluent gas can also be a ventilator, air pump, blower, or other mechanical device that moves breathable air.

The NO gas from the NO gas source 8 and the diluent gas from the diluent gas source 14 preferably pass through pressure regulators 16 to reduce the pressure of gas that is admitted to the NO delivery device 2. The respective gas streams pass via tubing 18 to a gas blender 20. The gas blender 20 mixes the NO gas and the diluent gas to produce a NO-containing gas that has a reduced concentration of NO compared to NO gas contained in the source 8. Preferably, a controller 36 controls the gas blender through electrical connection line 42 such that gas blender can be set to mix the gases to the desired NO concentration (e.g., 160 ppm-200 ppm for the high concentration period, and 20-40 ppm for the low concentration period) and output via tubing 24.

An optional flow control valve 22 can be located downstream of the gas blender 20 to control the flow of the NO gas to the delivery interface 6. The flow control valve 22 can include, for example, a proportional control valve that opens (or closes) in a progressively increasing (or decreasing if closing) manner. As another example, the flow control valve 22 can include a mass flow controller. The flow control valve 22 controls the flow rate of the NO-containing gas that is input to the delivery device 6.

The delivery interface 6 can be any type of interface adaptable for delivery of the gas to a mammal. For example, if the NO gas is to be delivered to the mammal's airways or lungs, the delivery interface 6 may include a facial mask, nasal insert, or endotracheal tube that interface with the mammal's respiratory system. It should be understood that the types of delivery interface 6 should not be limiting and depends on the specific applications and locations for the delivery of the gas. In another example, if the NO gas is to be delivered topically to a surface of the body such as a skin or eye, a surface of an organ such heart, stomach, etc., a bathing unit as described in U.S. Pat. No. 6,432,077, issued to one of the inventors may be used. U.S. Pat. No. 6,432,077 is hereby incorporated by reference as if fully set forth herein. Still further example of a delivery interface 6 may an interface to a dialysis circuit or extracorporeal circuitry wherein the NO gas is delivered directly to the blood or body fluids so as to expose the blood or body fluids to NO gas. Such delivery interface are described, for example, in U.S. patent application Ser. No. 10/658,665, filed on Sep. 9, 2003, which is hereby incorporated by reference in its entirety.

Still referring to FIG. 11, the delivery device 2 preferably includes a controller 36 that is capable of controlling the flow control valve 22 and the gas blender 20. The controller 36 is preferably a microprocessor-based controller 36 that is connected to an input device (not shown). The input device may be used by an operator to adjust various parameters of the delivery device such as NO concentration and therapy/exposure time periods. An optional display can also be connected with the controller 36 to display measured parameters and settings such as the set-point NO concentration, the concentration of NO flowing to the delivery interface 6, the concentration of NO2, the flow rate of gas into the delivery interface 6, the total time of therapy/delivery, and/or the number of cycles for alternating between high and low concentrations of NO gas.

Figure 14:
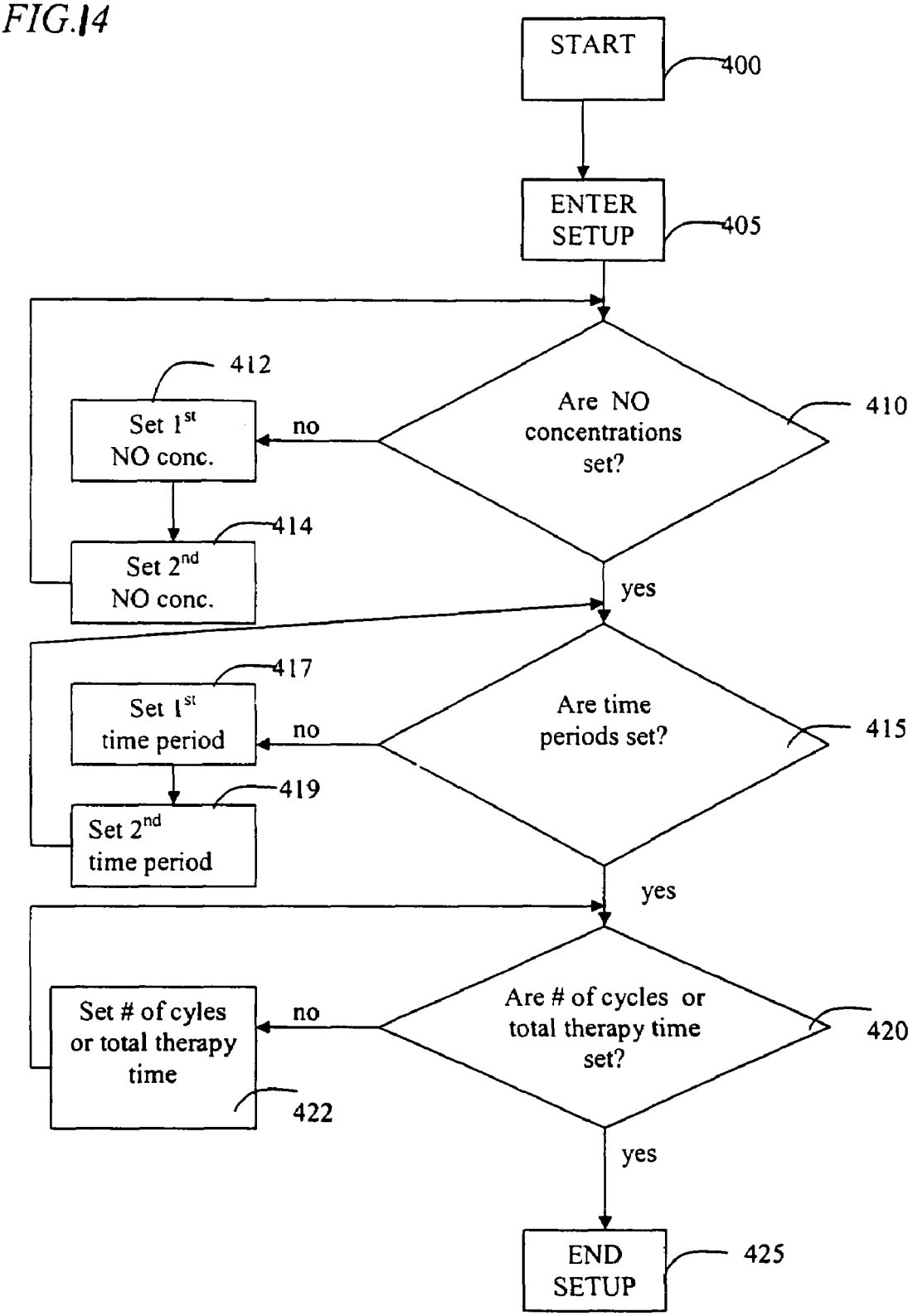
FIG. 14 illustrates the logic for setting the alternating delivery profile for high and low concentrations of nitric oxide gas.

The controller preferably includes a timer for counting down the time periods of the NO gas delivery at the different concentrations. Moreover, the controller preferably includes logic such as firmware or software programs for executing the alternate delivery of high and low concentration of NO gas at pre-set or user programmable time periods. The processes for execution by such logic are illustrated in FIGS. 14 and 15.

The controller 36 also preferably receives signals through signal line 48 from NO analyzer 40 regarding gas concentrations if such analyzer 40 are present within the delivery device 2. Signal lines 42 and 44 are connected to the gas blender 20 and flow control valve 22 respectively for the delivery and receipt of control signals.

In another embodiment of the nitric oxide delivery device, the controller 36 may be eliminated entirely and the gas blender 20 may be set manually at the desired high or low concentration of nitric oxide gas. The time period may also be tracked manually and at the appropriate set time period, the gas blender is adjusted to either increase to the high concentration NO gas or decrease to the low concentration NO gas. The flow rate of the gas into the delivery interface 6 may be pre-set or adjusted manually.

FIG. 12 shows an alternative embodiment of a nitric oxide delivery device 52 in which the desired concentration of NO gas is achieved by mixing with a T or Y shaped connection 70 based on the flow rates of the NO gas flowing from the NO gas source 8 and the diluent gas flowing from the diluent gas source 74. The respective flow rates are controlled via the flow control valves 72 and 75. Mixing of the gases starts at the T or Y shaped connection point 70 and continues through the delivery line 78. An NO analyzer 80 samples the gas mixture at a juncture close to the delivery interface to determine the NO concentration of the gas mixture flowing to the delivery interface 76. The measured NO concentration is then fed back through signal line 88 to the controller 86, which in turn processes the information by comparing the measured NO concentration with the set desired NO gas concentration. The controller 86 then adjusts the flow control valves 72 and 75, if appropriate, by sending control signals through lines 82 and 84 such that the flow rate(s) may be adjusted in order to achieve the desired concentration of NO gas flowing to the delivery interface 76. It should be understood that the controller 86 may similarly include all the features discussed above in connection with controller 36 in FIG. 11. Likewise, the delivery interface 76 may be adapted similarly to the delivery interface 6, as described in connection with FIG. 11.

FIG. 13 illustrates yet another embodiment of a nitric oxide delivery device in accordance to one aspect of the present invention. In this delivery device 102, instead of having gas mixers (e.g., gas blender or T or Y-shaped connection), the delivery device 102 utilizes a switch valve 104 to switch between a high concentration NO gas source 106 and a low concentration NO gas source 108. The switch valve 104 is controlled by the controller 116 that at the appropriate time switches between the high and low concentration of NO gas according to the present invention. It should be understood that the low concentration NO gas source 108 can also be replaced with non-NO gas source such as air, if the desired period of low NO concentration is zero ppm of NO gas.

Referring now to FIGS. 14 and 15, process flows are exemplified that may be executed by logic (firmware or software) programmed into the controllers 36, 86, and 116. FIG. 14 illustrates a process flow for setting up the desired concentrations and time periods for NO gas delivery starting from Step 400 "START." At Step 405, the logic enters the setup subroutine for setting the desired NO concentrations and time periods. At Step 410, the logic verifies if there are concentration values set for the NO delivery profile. If values are already set, then the process proceeds to Step 415 to verify the values set for the time periods of delivery. If no values have yet been set for the NO concentrations, then the logic calls a subprocess comprising of steps 412 and 414 is called to set the 1st and 2nd NO concentration for the therapeutic profile to be delivered. For example, the 1st NO concentration may be set for about 160 ppm to 300 ppm of NO gas to be delivered and the 2nd concentration may be set for 0 ppm to 80 ppm of NO gas to be delivered. The values of the NO concentrations set are then used by the controller to set the gas blender or the flow control valves in the process illustrated in FIG. 15.

After the values of NO concentrations have been set, the logic then proceeds to set the time periods for the delivery of the NO gas in Step 415. If the time periods have not yet been set, then a subprocess comprising steps 417 and 149 is called in which a first time period corresponding to the 1st NO concentration and a 2nd time period corresponding to the NO concentration are set.

After the values of NO concentrations and the time periods have been set, the logic then proceeds to set the number of cycles of alternating 1st and 2nd concentration of NO gas to be delivered. Alternatively, a total therapy time can be set in which the delivery of NO gas will cease at the end of the total therapy time. If the total therapy time or number of cycles have not been set, then a subprocess comprising of step 422 is called and these values are set. Afterwards, the setup process is ended and the device is ready to deliver NO gas for therapy.

FIG. 15 illustrates a process flow for execution by the logic in controller 36, 56, and 116, for the alternating delivery of high and low concentration of NO gas.

The START THERAPY in step 500 can be started once the NO gas delivery values in FIG. 14 has been entered. At Step 505, the controller 36 (FIG. 11) may then send a control signal through line 42 to the gas blender to set the appropriate gas blender settings to achieve the 1st concentration of NO gas, the value of which was set in the setup process of FIG. 14. This process may also include feedback control from the NO analyzer 40 (FIG. 11) to the controller 36 such that the control of the gas blender may be fine tuned in that the actual NO gas concentration being delivered to the delivery interface 6 matches the set NO gas concentration.

Alternatively, the controller at Step 505 may send control signals to the flow control valves 72 and 75 (FIG. 12) to set the appropriate flow rates for the mixing of the gases to achieve the 1st concentration set in the setup process of FIG. 14. This process may similarly include feedback control from the NO analyzer 80 (FIG. 12) to the controller 56. In yet another embodiment, the controller at Step 505 may set the switch valve 104 (FIG. 13) to select for delivery the NO gas from a source corresponding to the 1st concentration of NO gas set in the setup process of FIG. 14.

Delivery of NO gas proceeds in accordance with the settings in Step 505. At step 510, the timer comprised in the controller 36, 56, or 116 compares the value of the 1st time period set in FIG. 14 with the actual countdown in time. If the time period has not elapsed, then the gas blender, flow control valves, or switch valve settings remain the same in Step 512. If the 1st time period has elapsed, then step 515 sets the gas blender, flow rates, or switch valve settings to that corresponding to the 2nd concentration of NO gas, the value of which was set in the process of FIG. 14. Delivery of NO gas then proceeds on the 2nd concentration until the 2nd time period elapsed.

At the completion of the second time period, the logic proceeds to step 525 inquiring into whether the set number of cycles of total therapy time has elapsed. If the set number of cycles or total therapy time has been reached, the therapy ends in Step 530. Otherwise, the process repeats steps 505, 510, 515, and 525.

While embodiments of the present invention have been shown and described, various modifications may be made without departing from the scope of the present invention, and all such modifications and equivalents are intended to be covered. Notably, the intermittent dosing methods and the logic for alternate delivery of nitric oxide at high and low concentrations of nitric oxide can be incorporated into any of the controller in the devices that deliver nitric oxide gas based on the patient's respiratory flow profile described above.

What is claimed is:

1. A method of delivering nitric oxide to a patient comprising the steps of:
   providing a source of nitric oxide-containing gas;
   providing a source of oxygen-containing gas;
   detecting the onset of inspiration;
   determining the inspiration flow profile for an individual breath;
   administering the oxygen-containing gas with a flow profile that tracks the inspiration flow profile; and
   administering the nitric oxide-containing gas with a flow profile that is proportionally less than the flow profile of the oxygen-containing gas throughout inspiration;
   wherein the nitric oxide-containing gas is cyclically administered to the patient at a first concentration ranging from about 80 ppm to about 400 ppm of nitric oxide for a first period of time and at a second concentration of nitric oxide lower than the first concentration for a second period of time.

2. A method according to claim 1, wherein the method further includes the step of monitoring the concentration of at least one of the gases selected from the group consisting of: oxygen, nitric oxide, and nitrogen dioxide.

3. A method according to claim 1, wherein the flow profile of the nitric oxide-containing gas reaches zero flow at a time near the end of the patient inspiration flow profile, and wherein when said flow reaches zero, the flow profile of the oxygen-containing gas is greater than zero.

4. A method according to claim 1, wherein the flow profile of the nitric oxide-containing gas is zero flow at the beginning of the patient inspiration flow profile, and wherein when said flow is zero, the flow profile of the oxygen-containing gas is greater than zero.

5. A method according to claim 1, wherein the flow profile of the nitric oxide-containing gas is zero at the beginning of the patient inspiration profile while the flow profile of the oxygen-containing gas is greater than zero, and wherein at a time near the end of the patient inspiration flow profile, the flow profile of the nitric oxide-containing gas is zero while the flow profile of the oxygen-containing gas is greater than zero.

6. A method according to claim 1, further comprising the step of truncating the flow profile of the nitric oxide-containing gas to zero near the end of patient inspiration.

7. A method of claim 1 wherein the second period of time is longer than the first period of time.

8. A method of claim 1 wherein the first concentration of nitric oxide ranges from about 160 ppm to about 300 ppm.

9. A method of claim 1 wherein the second concentration of nitric oxide ranges from about 20 ppm to about 40 ppm.

10. A method of claim 1 wherein the first period of time is about 30 minutes and the second period of time is about 3.5 hours.

11. A method of delivering nitric oxide to a mammal, the method comprising the step of administering to a mammal a first concentration of nitric oxide gas for a number of time periods that are interspersed with intervals wherein a second concentration of nitric oxide gas is administered during the intervals; wherein the administration of the nitric oxide gas is at a flow profile that is less than a flow profile of an oxygen-containing gas, and the flow profile of the oxygen-containing gas being administered to the patient tracks an inspiration flow profile of the patient; and wherein the difference between the flow profile of the oxygen-containing gas and the flow profile of the nitric oxide gas progressively increases throughout inspiration.

12. A device for delivering nitric oxide to a patient comprising:
a source of an oxygen-containing gas connected via tubing to a patient inspiration interface device;
a source of a nitric oxide-containing gas connected via tubing to the patient inspiration interface device;
a first proportional flow controller located between the source of oxygen-containing gas and the patient inspiration interface device for varying the flow rate of the oxygen-containing gas to the patient inspiration interface device;
a second proportional flow controller located between the source of nitric oxide-containing gas and the patient inspiration interface device for varying the flow rate of the nitric oxide-containing gas to the patient inspiration interface device;
an inspiration flow profile sensor that measures the inspiration flow profile of the inspiration breath of the patient; and
a controller for controlling the first and second proportional flow controllers in response to the inspiration flow profile from the inspiration flow profile sensor, the first and second proportional flow controllers being controlled such that the oxygen-containing gas has a flow profile that tracks the inspiration flow profile, and wherein the nitric oxide-containing gas has a flow profile that is proportionally less than the oxygen-containing gas throughout inspiration; and
wherein the controller comprises logic for setting a nitric oxide delivery profile comprising at least two different concentrations of nitric oxide-containing gas and for automatically switching between the at least two different concentrations of nitric oxide-containing gas on a timed basis.

13. A device for delivering nitric oxide to a patient comprising:
a source of an oxygen-containing gas connected to a patient inspiration limb;
a source of a nitric oxide-containing gas connected to the patient inspiration limb;
a first proportional flow controller located between the source of oxygen-containing gas and the patient for varying the flow rate of the oxygen-containing gas to the patient;
a second proportional flow controller located between the source of nitric oxide-containing gas and the patient for varying the flow rate of the nitric oxide-containing gas to the patient;
a controller including instructions for the inspiration flow profile, the controller further controlling the first and second proportional flow controllers in response to the inspiration flow profile, the first and second proportional flow controllers being controlled such that the oxygen-containing gas has a flow profile that tracks the inspiration flow profile, and wherein the nitric oxide-containing gas has a flow profile that is proportionally less than the oxygen-containing gas throughout inspiration; and
wherein the controller comprises logic for setting a nitric oxide delivery profile comprising at least two different concentrations of nitric oxide-containing gas and for automatically switching between the at least two different concentrations of nitric oxide-containing gas on a timed basis.

14. A device for delivering nitric oxide to a patient comprising:
a source of an oxygen-containing gas connected to a patient inspiration limb;
a source of a nitric oxide-containing gas connected to the patient inspiration limb;
a first proportional flow controller located between the source of oxygen-containing gas and the patient for varying the flow rate of the oxygen-containing gas to the patient;
a second proportional flow controller located between the source of nitric oxide-containing gas and the patient for varying the flow rate of the nitric oxide-containing gas to the patient;
a controller including instructions for the inspiration flow profile, the controller further controlling the first and second proportional flow controllers in response to the inspiration flow profile, the first and second proportional flow controllers being controlled such that the oxygen-containing gas has a flow profile that tracks the inspiration flow profile, and wherein the nitric oxide-containing gas flow profile is less than, but closely tracks the oxygen-containing gas flow profile in the beginning of the inspiration, wherein the difference between the flow profiles of the oxygen-containing gas and the nitric oxide-containing gas progressively increases through the remainder of inspiration; and
wherein the controller comprises logic for setting a nitric oxide delivery profile comprising at least two different concentrations of nitric oxide-containing gas and for automatically switching between the at least two different concentrations of nitric oxide-containing gas on a timed basis.

15. A device for delivering nitric oxide to a patient who is mechanically-ventilated comprising:
a source of an oxygen-containing gas connected to a patient inspiration limb;
a source of a nitric oxide-containing gas connected to the patient inspiration limb;
a first proportional flow controller located between the source of oxygen-containing gas and the patient for varying the flow rate of the oxygen-containing gas to the patient;
a second proportional flow controller located between the source of nitric oxide-containing gas and the patient for varying the flow rate of the nitric oxide-containing gas to the patient;
a controller including instructions for the inspiration flow profile, the controller further controlling the first and second proportional flow controllers in response to the inspiration flow profile, the first and second proportional flow controllers being controlled such that the oxygen-containing gas has a flow profile that tracks the inspiration flow profile, and wherein the nitric oxide-containing gas has a flow profile that is substantially less than the oxygen-containing gas flow profile at the beginning of inspiration, and wherein the difference between the flow profile of the oxygen-containing gas and the nitric oxide-containing gas progressively decreases throughout the remainder of inspiration; and wherein the controller comprises logic for setting a nitric oxide delivery profile comprising at least two different concentrations of nitric oxide-containing gas and for automatically switching between the at least two different concentrations of nitric oxide-containing gas on a timed basis.

16. A device for delivering nitric oxide to a spontaneous-breathing patient comprising:

a source of an oxygen-containing gas connected via tubing to a patient inspiration interface device;

a source of a nitric oxide-containing gas connected via tubing to the patient inspiration interface device;

a first proportional flow controller located between the source of oxygen-containing gas and the patient inspiration interface device for varying the flow rate of the oxygen-containing gas to the patient inspiration interface device;

a second proportional flow controller located between the source of nitric oxide-containing gas and the patient inspiration interface device for varying the flow rate of the nitric oxide-containing gas to the patient inspiration interface device;

an inspiration flow profile sensor that measures the inspiration flow profile of the inspiration breath of the patient; and a controller for controlling the first and second proportional flow controllers in response to the inspiration flow profile from the inspiration flow profile sensor, the first and second proportional flow controllers being controlled such that the oxygen-containing gas has a flow profile that tracks the inspiration flow profile, and wherein the nitric oxide-containing gas has a flow profile that is substantially less than the oxygen-containing gas flow profile at the beginning of inspiration, and wherein the difference between the flow profile of the oxygen-containing gas and the nitric oxide-containing gas progressively decreases throughout the remainder of inspiration; and wherein the controller comprises logic for setting a nitric oxide delivery profile comprising at least two different concentrations of nitric oxide-containing gas and for automatically switching between the at least two different concentrations of nitric oxide-containing gas on a timed basis.

17. A device for delivering nitric oxide to a spontaneous-breathing patient comprising:

a source of an oxygen-containing gas connected via tubing to a patient inspiration interface device;

a source of a nitric oxide-containing gas connected via tubing to the patient inspiration interface device;

a first proportional flow controller located between the source of oxygen-containing gas and the patient inspiration interface device for varying the flow rate of the oxygen-containing gas to the patient inspiration interface device;

a second proportional flow controller located between the source of nitric oxide-containing gas and the patient inspiration interface device for varying the flow rate of the nitric oxide-containing gas to the patient inspiration interface device;

an inspiration flow profile sensor that measures the inspiration flow profile of the inspiration breath of the patient; and a controller for controlling the first and second proportional flow controllers in response to the inspiration flow profile from the inspiration flow profile sensor, the first and second proportional flow controllers being controlled such that the oxygen-containing gas has a flow profile that tracks the inspiration flow profile, and wherein the nitric oxide-containing gas has a flow profile that is less than, but closely tracks the oxygen-containing gas flow profile in the beginning of the inspiration, wherein the difference between the flow profiles of the oxygen-containing gas and the nitric oxide-containing gas progressively increases through the remainder of inspiration; and wherein the controller comprises logic for setting a nitric oxide delivery profile comprising at least two different concentrations of nitric oxide-containing gas and for automatically switching between the at least two different concentrations of nitric oxide-containing gas on a timed basis.

* * * * *